(12) United States Patent
Pathak et al.

(10) Patent No.: US 6,923,986 B2
(45) Date of Patent: Aug. 2, 2005

(54) MULTIBLOCK BIODEGRADABLE HYDROGELS FOR DRUG DELIVERY AND TISSUE TREATMENT

(75) Inventors: Chandrashekhar P. Pathak, Austin, TX (US); Shikha P. Barman, Bedford, MA (US); C. Michael Philbrook, Boston, MA (US); Amarpreet S. Sawhney, Lexington, MA (US); Arthur J. Coury, Boston, MA (US); Luis Z. Avila, Arlington, MA (US); Mark T. Kieras, Burlingame, CA (US)

(73) Assignee: Genzyme Corporation, Cambridge, MA (US)

(*) Notice: Subject to any disclaimer, the term of this patent is extended or adjusted under 35 U.S.C. 154(b) by 0 days.

(21) Appl. No.: 10/650,163

(22) Filed: Aug. 27, 2003

(65) Prior Publication Data

US 2004/0072961 A1 Apr. 15, 2004

Related U.S. Application Data

(62) Division of application No. 10/114,722, filed on Apr. 2, 2002, now Pat. No. 6,639,014, which is a continuation of application No. 09/710,416, filed on Nov. 9, 2000, now Pat. No. 6,410,645, which is a division of application No. 08/692,914, filed on Jul. 26, 1996, now Pat. No. 6,201,065.
(60) Provisional application No. 60/001,723, filed on Jul. 28, 1995.

(51) Int. Cl.⁷ ..................... A61K 31/765; A61K 9/107; C08L 53/00
(52) U.S. Cl. .................... 424/486; 424/487; 424/78.06; 424/DIG. 13; 524/504; 524/505; 524/916; 525/79; 525/90; 525/93; 525/383; 525/941
(58) Field of Search ........................... 525/383, 79, 90, 525/93, 941; 524/504, 505, 916; 424/486, 487, 78.06, DIG. 13

(56) References Cited

U.S. PATENT DOCUMENTS

| | | |
|---|---|---|
| 3,931,148 A | 1/1976 | Langdon |
| 3,931,337 A | 1/1976 | Langdon |
| 3,954,886 A | 5/1976 | Langdon |
| 4,072,704 A | 2/1978 | Langdon |
| 4,178,434 A | 12/1979 | Langdon |
| 4,189,609 A | 2/1980 | Langdon |
| 4,191,820 A | 3/1980 | Langdon |
| 4,261,704 A | 4/1981 | Langdon |
| 4,281,199 A | 7/1981 | Langdon |
| 4,287,078 A | 9/1981 | Langdon et al. |
| 4,314,000 A | 2/1982 | Thir et al. |
| 4,408,084 A | 10/1983 | Langdon |
| 4,504,418 A | 3/1985 | Langdon |
| 4,519,950 A | 5/1985 | Langdon |
| 4,526,938 A | 7/1985 | Churchill et al. |
| 4,716,203 A | 12/1987 | Casey et al. |
| 4,741,337 A | 5/1988 | Smith et al. |
| 4,757,128 A | 7/1988 | Domb et al. |
| 4,789,724 A | 12/1988 | Domb et al. |
| 4,818,542 A | 4/1989 | DeLuca et al. |
| 4,826,945 A | 5/1989 | Cohn et al. |
| 4,857,311 A | 8/1989 | Domb et al. |
| 4,888,176 A | 12/1989 | Langer et al. |
| 4,938,763 A | 7/1990 | Dunn et al. |
| 4,957,744 A | 9/1990 | della Valle et al. |
| 4,987,744 A | 1/1991 | Handley et al. |
| 5,078,994 A | 1/1992 | Nair et al. |
| 5,145,518 A | 9/1992 | Winnik et al. |
| 5,160,745 A | 11/1992 | DeLuca et al. |
| 5,213,580 A | 5/1993 | Slepian et al. |
| 5,219,564 A | 6/1993 | Zalipsky et al. |
| 5,296,627 A | 3/1994 | Tang et al. |
| 5,328,471 A | 7/1994 | Slepian |
| 5,403,893 A | 4/1995 | Tanaka et al. |
| 5,410,016 A | 4/1995 | Hubbell et al. |
| 5,415,864 A | 5/1995 | Kopecek et al. |
| 5,417,983 A | 5/1995 | Nagase et al. |
| 5,418,301 A | 5/1995 | Hult et al. |
| 5,429,826 A | 7/1995 | Nair et al. |
| 5,496,581 A | 3/1996 | Yianni et al. |
| 5,508,317 A | 4/1996 | Müller |
| 5,510,103 A | 4/1996 | Yokoyama et al. |
| 5,512,091 A | 4/1996 | Steiner |
| 5,525,657 A | 6/1996 | Anchor et al. |
| 5,858,746 A | 1/1999 | Hubbell et al. |

FOREIGN PATENT DOCUMENTS

| | | |
|---|---|---|
| DE | 1 595 369 | 4/1970 |
| EP | 0 552 802 A3 | 7/1993 |
| EP | 0 552 802 A2 | 7/1993 |
| EP | 0 108 933 A1 | 5/1994 |
| WO | WO 93/17669 A1 | 9/1993 |
| WO | WO 94/21324 A1 | 9/1994 |
| WO | WO 97/15287 A1 | 5/1997 |

OTHER PUBLICATIONS

Alexandridis, et al., "Micellization of Poly(ethylene oxide)–Poly(propylene oxide)–Poly(ethylene oxide) Triblock Copolymers in Aqueous Solutions: Thermodynamics of Copolymer Association," *Macromolecules* 27(9):2414 (1994).

Asano, et al., "Fluorescence Studies of Dansyl–Labeled Poly(N–isopropylacrylamide) Geis and Polymers in Mixed Water/Methanol Solutions," *Macromolecules* 28:5861–5866 (1995).

Bae, et al., "On–Off" Thermocontrol of Solute Transport. I. Temperature Dependence of Swelling of N–Isopropylacrylamide Networks Modified with Hydrophobic Components in Water, *Pharmaceutical Research* 8(4):531–537 (1991).

(Continued)

*Primary Examiner*—Tae H. Yoon
(74) *Attorney, Agent, or Firm*—Isabelle A. S. Blundell

(57) ABSTRACT

Gel-forming macromers including at least four polymeric blocks, at least two of which are hydrophobic and at least one of which is hydrophilic, and including a crosslinkable group are provided. The macromers can be covalently crosslinked to form a gel on a tissue surface in vivo. The gels formed from the macromers have a combination of properties including thermosensitivity and lipophilicity, and are useful in a variety of medical applications including drug delivery and tissue coating.

13 Claims, 8 Drawing Sheets

OTHER PUBLICATIONS

Birrenbach, et al., "Polymerized Micelles and Their Use as Adjuvants in Immunology," *J. Pharm. Sci.* 65(12):1763–1766 (1976).

Chen, et al., "Novel Graft Copolymers Of A Temperature–Sensitive Polymer Grafted To A pH–Sensitive, Bioadhesive Polymer For Controlled Drug Delivery", *21st Annual Meeting Of The Society For Biomaterials* (1995).

Couvreur, et al., "Nanocapsules: A New Type of Lysosomotropic Carrier," *FEBS Letters* 84(2):323–326 (1977).

Desai, et al., "Surface Modifications of Polymeric Biomaterials for Reduced Thrombogenicity," *Polym. Mater. Sci. Eng.* 62:731–735 (1991).

Desai, et al., "Tissue Response to Intraperitoneal Implants of Polyethylene Oxide–Modified Polyethylene Terephthalate," submitted to *Biomaterials* pp. 1–12.

Domb, et al., "Poly(anhydridges). 3. Poly(anhydrides) Based on Aliphatic–Aromatic Diacids," *Macromolecules* 22(8):3200–3204 (1989).

Heller, et al., Biodegradable Polymers as Drug Delivery Systems, Chasin, M. and Langer, R., eds., (Marcel Dekker, Inc., New York, 1990) (Table of Contents).

Hil–West, et al., "Prevention of Postoperative Adhesions in the Rat by In Situ Photopolymerization of Bioresorbable Hydrogel Barriers," *Obsterics & Gynecology* 83(1):59–64 (1994).

Hoffman, et al., "Applications of Thermally Reversible Polymers and Hydrogels in Therapeutics and Diagnostics," *J. Controlled Release* 6:297–305 (1987).

Holland, et al., "Polymers for Biodegradable Medical Devices. 1. The Potential of Polyesters as Controlled Macromolecular Release Systems," *Controlled Release* 4(3):155–180 (1986).

Ishizu, et al., "Core–Shell Type Polymer Microspheres Prepared from Block Copolymers," *J. Polymer Science: Part C: Polymer Letters* 26:281–286 (1988).

Kataoka, et al., "Block copolymer micelles as vehicles for drug delivery," *J. Controlled Release* 24(1–3):119–132 (1993).

Kulkarni, et al., "Polylatic Acid for Surgical Implants," *Arch. Surg.* 93(5):839–843 (1966).

Marsh, et al., "Lipid–Absorbing Polymers," *JPL Quarterly Technical Review* 2(4):1–6 (1974).

Nagaoka, et al., "Interaction Between Blood Components and Hydrogels with Poly(Oxyethylene) Chains," *Polymers As Biomaterials*, (Shalaby, ed.), pp. 361–374 (Plenum Press, New York and London).

Park, et al., "Synthesis of microphased core–corona type microgel," *Polymer Commun.* 29:230–231 (1988).

Rolland, et al., "New Macromolecular Carriers for Drugs. I. Preparation and Characterization of Poly(oxyethylene–$b$–isoprene–$b$–oxyethylene) Blocke Copolymer Aggregates," *J. App. Polymer Sci.* 44:1195–1203 (1992).

Sawhney, et al., "Bioerodible Hydrogels Based on Photopolymerized Poly(ethylene glycol)–co–poly($\alpha$–hydroxy acid) Diacrylate Macromers," *Macromolecules* 26(4):581–587 (1993).

Sawhney, et al., "Rapidly degraded terpolymers of di–lactide, glyoolide, and __–caprolactone with increased hydrophilicity by copolymerization with polyethers," *J. Biomed. Mater. Res.* 24(10):1397–1411 (1990).

Sawhney, et al., *The 21st Annual Meeting of the Society for Biomaterials*, (San Francisco, CA, 1995).

Spilizewski, et al., "In Vitro Apparatus for Controlled Release Studies and Intrinsic Rate of Permeation," *J. Control. Rel.* 1(3):197–203 (1985).

Tanaka, et al., "Immobilization of Yeast Microbodies by Inclusion with Photo–crosslinkable Resins," *Eur. J. Biochem.* 80:193–197 (1977).

Wilson, et al., "Photochemical Stabilization of Block Copolymre Micelles," *Eur. Polym. J.* 24(7):617–621 (1988).

Yokoyama, et al., "Polymer Micelles as Novel Drug Carrier: Adriamycin–Conjugated Poly(ethylene Glycol)–Poly(aspartic Acid) Block Copolymer," *J. Controlled Release* 11:269–278 (1990).

PEG-Caproate-Glycolate-Acrylate, n =182
Monomer A: p=4, q=1; Monomer B: p=3, q=2;
Monomer C: p=2, q=3; Monomer D: p=1, q=4
p and q are randomly distributed
Structure of macromonomers

MULTIBLOCK BIODEGRADABLE HYDROGELS FOR DRUG DELIVERY AND TISSUE TREATMENT

BACKGROUND OF THE INVENTION

This application is a divisional application of U.S. Ser. No. 10/114,722 filed on Apr. 2, 2002 now issued as U.S. Pat. No. 6,639,014, which is a continuation of application U.S. Ser. No. 09/710,416 filed on Nov. 9, 2000 now issued as U.S. Pat. No. 6,410,645, which is a divisional of application U.S. Ser. No. 08/692,914 filed on Jul. 26, 1996 now issued as U.S. Pat. No. 6,201,065 which claims the benefit of priority to provisional application U.S. Ser. No. 60/001,723 filed on Jul. 28, 1995.

The present invention is generally in the area of biodegradable polymers for use in drug delivery and biomedical applications.

Biodegradable polymers have been developed for use in a variety of surgical and drug delivery applications. The synthesis and biodegradability of poly(lactic acid) was reported by Kulkarni et al., *Arch. Surg.*, 93:839 (1966). Biodegradable polyanhydrides and polyorthoesters having labile backbone linkages have been developed. Domb et al., *Macromolecules*, 22:3200 (1989); and Heller et al., "Biodegradable Polymers as Drug Delivery Systems," Chasin, M. and Langer, R., Eds., Dekker, New York, 121–161 (1990), the disclosures of which are incorporated herein. Polymers which degrade into naturally occurring materials, such as polyaminoacids, also have been developed. Polyesters of α-hydroxy acids, such as lactic acid or glycolic acid, are widely used as biodegradable materials for applications ranging from closure devices, including sutures and staples, to drug delivery systems. Holland et al., *Controlled Release*, 4:155–180, (1986); U.S. Pat. No. 4,741,337 to Smith et al.; and Spilizewski et al., *J. Control. Rel.*, 2:197–203 (1985), the disclosures of which are incorporated herein.

Degradable polymers containing water-soluble polymer elements have been described. Degradable polymers have been formed by copolymerization of lactide, glycolide, and ε-caprolactone with the polyether, polyethylene glycol ("PEG"), to increase the hydrophilicity and degradation rate. Sawhney et al., *J. Biomed. Mater. Res.* 24:1397–1411 (1990). U.S. Pat. No. 4,716,203 to Casey et al. describes the synthesis of a block copolymer of PGA (poly(glycolic acid)) and PEG. U.S. Pat. No. 4,716,203 to Casey et al. describes the synthesis of PGA-PEG diblock copolymers.

Polymers formed from crosslinkable monomers or prepolymers have been developed in the prior art. Crosslinked hyaluronic acid has been used as a degradable swelling polymer for biomedical applications. U.S. Pat. Nos. 4,987,744 and 4,957,744 to Della Valle et al.; and Della Valle et al., *Polym. Mater. Sci. Eng.*, 62:731–735 (1991).

U.S. Pat. No. 5,410,016 to Hubbell et al., the disclosure of which in incorporated herein, discloses the in situ crosslinking of biodegradable, water-soluble macro-monomers, ("macromers") to form barrier coatings and matrices for delivery of biologically active agents. Other polymers for drug delivery or other biomedical applications are described in U.S. Pat. No. 4,938,763 to Dunn, U.S. Pat. Nos. 5,160,745 and 4,818,542 to DeLuca, U.S. Pat. No. 5,219,564 to Zalipsky, U.S. Pat. No. 4,826,945 to Cohn, and U.S. Pat. Nos. 5,078,994 and 5,429,826 to Nair, the disclosures of which are incorporated herein by reference. Methods for delivery of the polymers materials include syringes (U.S. Pat. No. 4,938,763 to Dunn et al.) spray applicators (WO 94/21324 by Rowe et al.) and catheter delivery systems (U.S. Pat. Nos. 5,328,471; and 5,213,580 to Slepian). The synthesis of macromers Including a central chain of polyethylene glycol, with an oligomeric hydroxyacid at each end and acrylic esters at the ends of the hydroxy acid oligomer also has been reported. Sawhney A. S. et al., *Macromolecules*, 26: 581 (1993); and PCT WO 93/17669 by Hubbell J. A. et al., the disclosures of which are incorporated herein by reference.

Thermal volume changes in polymeric gels, such as esters and amides of polyacrylic acid, have been described. For example, poly(N-isopropyl acrylamide) based hydrogels, which are thermosensitive in aqueous systems, have been used for controlled drug delivery and other applications. U.S. Pat. No. 5,403,893 to Tanaka et al.; and Hoffman A. S. et al., *J. Controlled Release*, 6:297 (1987), the disclosures of which are incorporated herein. Poly(N-isopropyl acrylamide), however, is non-degradable and is not suitable for applications where biodegradable polymers are required. Non-biodegradable polymeric systems for drug delivery are disadvantageous since they require removal after the drug-polymer device is implanted.

It is an object of the invention to provide improved polymer systems for use in drug delivery and other biomedical applications such as surgical applications. It is an additional object of the invention to provide polymer systems for use in controlled drug delivery which are capable of releasing a biologically active agent in a predictable and controlled rate. It is a further object of the invention to provide polymers for use in controlled drug delivery which release the active agent locally at a particular targeted site where it is needed. It is another object of the invention to provide polymer systems for use in drug delivery which have properties including volume and drug release which are variable with temperature or other parameters such as pH or ion concentration.

SUMMARY OF THE INVENTION

Macromers are provided which are capable of gelling in an aqueous solution. In one embodiment, the macromers include at least four polymeric blocks, at least one of which is hydrophilic and at least two of which are hydrophobic, and include a crosslinkable group. The polymer blocks may be selected to provide macromers with different selected properties. The macromers can be covalently crosslinked to form a gel on a tissue surface in vivo. The gels formed from the macromers have a combination of properties including thermosensitivity and lipophilicity, and are useful in a variety of medical applications including drug delivery and tissue coating.

DETAILED DESCRIPTION OF THE INVENTION

Figure 1:
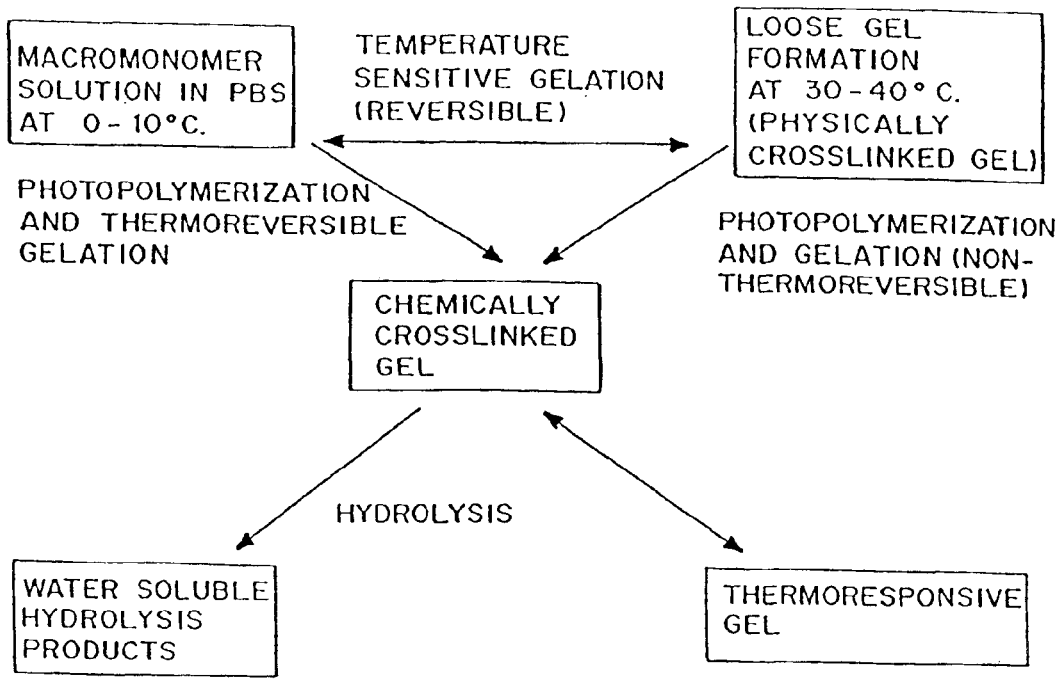
FIG. 1 is a scheme showing the different gel states and properties of one embodiment of a thermoresponsive biodegradable macromer formed from a polypropylene oxide-polyethylene oxide block copolymer.

Macromers are provided which are crosslinkable to form hydrogels which are useful as matrices for controlled drug delivery. In a preferred embodiment, biodegradable macromers are provided in a pharmaceutically acceptable carrier, and are capable of crosslinking, covalently or noncovalently, to form hydrogels which are thermoresponsive. A biologically active agent may be incorporated within the macromer solution or in the resulting hydrogel after crosslinking. The hydrogels have properties, such as volume and drug release rate, which are dependent upon temperature. The hydrogels may be formed in situ, for example, at a tissue site, and may be used for for controlled delivery of bioactive substances and as tissue coatings. The macromers used to form the hydrogels may be fabricated with domains having specific properties including selected hydrophobicity, hydrophilicity, thermosensitivity or biodegradability, and combinations thereof.

Macromers

The macro-monomers ("macromers") which are ionically or covalently crosslinkable to form hydrogels preferably consist of a block copolymer. The macromers can be quickly polymerized from aqueous solutions. The macromers are advantageously capable of thermoreversible gelation behavior, and preferably may be polymerized in a solution state or in a gel state. The macromers are defined as including a hydrophilic block capable of absorbing water, and at least one block, distinct from the hydrophilic block, which is sufficiently hydrophobic to precipitate from, or otherwise change phase while within, an aqueous solution, consisting of water, preferably containing salts, buffers, drugs or polymerizing reagents, at temperatures within or near the physiologically compatible range, for example 0 to 65° C. The hydrophilic block optionally may be an amphiphilic block. The macromer may include more than one of the same or different hydrophilic or hydrophobic region. Preferably, the macromers include at least three blocks, or more preferably four blocks.

The block copolymers may be linear (AB, ABA, ABABA or ABCBA type), star (AnB or BAnC, where B is at least n-valent, and n is 3 to 6) or branched (multiple A's depending from one B). In these formulae, either A or B may be the hydrophilic block, and the other the amphipathic or hydrophilic block, and the additional block C may be either.

In another embodiment, the macromer includes at least four covalently-linked polymeric blocks, wherein: at least one, or in another embodiment, at least two blocks are hydrophilic, and the hydrophilic blocks individually have a water solubility of at least 1 gram/liter; at least two blocks are sufficiently hydrophobic to aggregate to form micelles in an aqueous continuous phase; and the macromer further includes at least one crosslinkable group. The crosslinkable groups optionally may be separated by at least one degradable linkage capable of degrading under physiological conditions. In one embodiment, at least one hydrophobic block may be separated from any reactive group by at least one hydrophilic block.

The macromer further may include five total blocks having the same or different properties such as thermal sensitivity, hydrophilicity or hydrophobicity. Each block also may have a combination of properties. For example, a block may be hydrophilic and also thermosensitive. Additionally, the multiblock macromer may include chemically distinct blocks or may incorporate more than one of the same identical block. The macromer is fabricated with a structure and with properties suitable for different applications. For example the macromer may include a central block of dimer fatty acid which includes central hydrocarbon chain of about 30 carbon atoms and two terminal carboxy groups which are esterified with a thermosensitive poloxamer, such as Pluronic L1050. This central molecule further is polylactated at each hydroxy terminus, and end capped with acryloyl chloride. An another embodiment is a poloxamer including polyhydroxy groups polymerized on each end, and wherein the molecule is end capped at each end with a reactive group such as an acrylate or a secondary isocyanate.

The configuration of the macromers may be preselected depending on the use of the macromer. The macromers may include at least two hydrophobic blocks, separated by a hydrophilic block. The macromers also may be fabricated with a crosslinkable group which is separated by a degradable group from any other crosslinkable group. One preferred embodiment is wherein the dry macromer absorbs at least about 10% in weight of water. The molecular weight of the macromer preferably is at least 1000 Daltons, or optionally is at least 2000 Daltons, or in an alternative embodiment, at least 4000 Daltons.

In a preferred embodiment, the macromer includes at least one thermally sensitive region, and an aqueous solution of the macromer is capable of gelling either ionically and/or by covalent crosslinking to produce a hydrogel with a temperature dependent volume. This permits the rate of release of a drug incorporated in the hydrogel to change depending upon the volume of the hydrogel. Useful macromers are those which are, for example, capable of thermoreversible gelation of an aqueous solution of the macromer at a concentration of at least 2% by weight, and wherein the gelation temperature is between about 0° C. and about 65° C. The macromer also may have a phase transition temperature in the range of 0 to 100° C., and wherein the transition temperature is affected by the ionic composition of an aqueous solution of the macromer or the concentration of macromer in the aqueous solution.

The macromers may be formed by modification of materials and methods described in the prior art. Macromers including a central chain of polyethylene glycol, with oligomeric hydroxy acid at each end and acrylic esters at the ends of the hydroxy acid oligomer are described in Sawhney A. S. et al., *Macromzolecules,* 26: 581 (1993); and PCT WO 93/17669 by Hubbell J. A. et al., the disclosures of which are incorporated herein by reference. U.S. Pat. No. 5,410,016 to Hubbell et al., the disclosure of which is incorporated herein by reference, discloses that biodegradable, water-soluble macromers can be crosslinked in situ to form barrier coatings and depots or matrices for delivery of biologically active agents such as therapeutic drugs. In addition to the materials and methods described in U.S. Pat. No. 5,410,016, materials and methods described by Dunn (U.S. Pat. No. 4,938,763), DeLuca (U.S. Pat. Nos. 5,160,745; and 4,818,542), Zalipsky (U.S. Pat. No. 5,219,564), Cohn (U.S. Pat. No. 4,826,945), Nair (U.S. Pat. Nos. 5,078,994; and 5,429,826), the disclosures of which are incorporated herein by reference, are useful to form the macromers described herein.

For example, the macromer may include a poloxamer backbone extended with hydrophobic materials, such as oligolactate moieties, which serve as the biodegradable segment of the molecule, wherein the PEO-PPO-PEO-lactate copolymer is terminated by acrylate moieties. The materials can be combined with, then delivered and photopolymerized in situ, onto target organs to conform to a specific shape.

The macromers and hydrogels formed therefrom preferably are biocompatible, preferably not causing or enhancing a biological reaction when implanted or otherwise administered within a mammal. The macromers, and any breakdown products of the hydrogels or macromers, preferably are not significantly toxic to living cells, or to organisms. The hydrogels also may have liquid crystalline properties for example at high concentration, which are useful in controlling the rate of drug delivery. Ionic properties can be provided in the backbone of the macromers, conferring the further property of control of delivery and/or physical state by control of the ionic environment, including pH, of the macromer or gel. In one embodiment, the critical ion composition is the hydrogen ion concentration. For example, when a poloxamine, such as a Tetronic surfactant, is used as the core of the macromer, then the resulting macromer has the ionic groups (amines) in the core, and the macromers' ability to gel upon changes in temperature is affected by the pH of the solution.

Thermosensitive Regions

The macromers may be provided with one or more regions which have properties which are thermoresponsive. As used herein, thermoresponsiveness is defined as including properties of a hydrogel, such as volume, transition from a liquid to a gel, and permeability to biologically active agents, which are dependent upon the temperature of the hydrogel In one embodiment, the macromers are capable of reversible gelation which is controlled by temperature. The reversible gel further optionally may be crosslinked in situ into an irreversibly and covalently crosslinked gel. This permits the macromer to be applied reliably in surgical applications on a specific area of tissue without running off or being washed off by body fluids prior to gelation or crosslinking.

In one preferred embodiment, the macromers are capable of gelling thermoreversibly, for example, due to the content of poloxamer regions. Since gelling is thermoreversible, the gel will dissipate on cooling. The macromers may further include crosslinkable groups which permit the gel to be further covalently crosslinked for example by photopolymerization. After crosslinking, the gels are irreversibly crosslinked. However, they retain other significant thermoresponsive properties, such as changes in volume and in permeability.

By appropriate choice of macromer composition, hydrogels can be created in situ which have thermosensitive properties, including volume changes and drug release which are dependent upon temperature, which can be used to control drug delivery from the hydrogel. Control of drug delivery can be further controlled by adjustment of properties such as hydrophobicity of amphiphilic or other regions in the gel. Change in volume of the hydrogel may readily be measured by examination of macroscopic unrestrained samples during temperature excursions. Changes in excess of 100% in volume may be obtained with hydrogels formed from the macromers, such as an acrylate-capped polyglycolide-derivatized poloxamer of about 30% PPO (polypropylene oxide) content, the expansion occurring gradually on change of the temperature from about 0° C. to body temperature (37° C.). Changes of more than 5% in any linear dimension may be effective in altering the release rate of a macromolecular drug.

The macromers preferably include thermogelling macromers, such as "poloxamers", i.e., poly(ethylene oxide)-poly(propylene oxide)-poly(ethylene oxide) ("PEO-PPO-PEO"), block copolymers. Aqueous polymeric solutions of poloxamers undergo microphase transitions at an upper critical solution temperature, causing a characteristic gel formation. This transition is dependent on concentration and composition of the block copolymer. Alexandridis et al., *Macromolecules,* 27:2414 (1994). The segmental polyether portion of the molecule gives water solubility and thermosensitivity. The material also advantageously have been demonstrated to be biocompatible.

For example, the macromer may include a poloxamer backbone extended with hydrophobic materials, such as oligolactate moieties, which serve as the biodegradable segment of the molecule, wherein the PEO-PPO-PEO-lactate copolymer is terminated by acrylate moieties. The materials can be combined with a bioactive agent, then delivered and photopolymerized in situ. In addition to poloxamer cores, meroxapols, such as "reversed Pluronics" (PPO-PEO-PPO copolymers) and poloxamines, such as Tetronic™ surfactants, may be used.

Other polymer blocks which may be provided in the monomer which are capable of temperature dependent volume changes include water soluble blocks such as polyvinyl alcohol, polyvinyl-pyrrolidone, polyacrylic acids, esters and amides, soluble celluloses, peptides and proteins, dextrans and other polysaccharides. Additionally, polymer blocks with an upper critical point may be used, such as other polyalkylene oxides, such as mixed polyalkylene oxides and esters, derivatized celluloses, such as hydroxypropylmethyl cellulose, and natural gums such as konjac glucomannan.

In another embodiment, the macromer is defined as having an optically anisotropic phase at a concentration at or below the maximal solubility of the macromer in an aqueous solution, at a temperature between about 0 and 65° C.

Crosslinkable Groups.

The macromers preferably include crosslinkable groups which are capable of forming covalent bonds with other compounds while in aqueous solution, which permit crosslinking of the macromers to form a gel, either after, or independently from thermally dependent gellation of the macromer Chemically or ionically crosslinkable groups known in the art may be provided in the macromers. The crosslinkable groups in one preferred embodiment are polymerizable by photoinitiation by free radical generation, most preferably in the visible or long wavelength ultraviolet radiation. The preferred crosslinkable groups are unsaturated groups including vinyl groups, allyl groups, cinnamates, acrylates, diacrylates, oligoacrylates, methacrylates, dimethacrylates, oligomethoacrylates, or other biologically acceptable photopolymerizable groups.

Other polymerization chemistries which may be used include, for example, reaction of amines or alcohols with isocyanate or isothiocyanate, or of amines or thiols with aldehydes, epoxides, oxiranes, or cyclic imines; where either the amine or thiol, or the other reactant, or both, may be covalently attached to a macromer. Mixtures of covalent polymerization systems are also contemplated. Sulfonic acid or carboxylic acid groups' may be used.

Preferably, at least a portion of the macromers will have more than one crosslinkable reactive group, to permit formation of a coherent hydrogel after crosslinking of the macromers. Up to 100% of the macromers may have more than one reactive group. Typically, in a synthesis, the percentage will be on the order of 50 to 90%, for example, 75 to 80%. The percentage may be reduced by addition of small co-monomers containing only one active group. A lower limit for crosslinker concentration will depend on the properties of the particular macromer and the total macromer concentration, but will be at least about 3% of the total molar concentration of reactive groups. More preferably, the crosslinker concentration will be at least 10%, with higher concentrations, such as 50% to 90%, being optimal for maximum retardation of many drugs. Optionally, at least part of the crosslinking function may be provided by a low-molecular weight crosslinker. When the drug to be delivered is a macromolecule, higher ranges of polyvalent macromers (i.e., having more than one reactive group) are preferred. If the gel is to be biodegradable, as is preferred in most applications, then the crosslinking reactive groups should be separated from each other by biodegradable links. Any linkage known to be biodegradable under in vivo conditions may be suitable, such as a degradable polymer block. The use of ethylenically unsaturated groups, crosslinked by free radical polymerization with chemical and/or photoactive initiators, is preferred as the crosslinkable group.

The macromer may also include an ionically charged moiety covalently attached to the macromer, which optionally permits gellation or crosslinking of the macromer.

Hydrophobic Regions

The macromers further may include hydrophobic domains. The hydrophobicity of the gel may be modified to alter drug delivery or three dimensional configuration of the gel. Amphiphilic regions may be provided in the macromers which in aqueous solution tend to aggregate to form micellar domain, with the hydrophobic regions oriented in the interior of these domains (the "core"), while the hydrophilic domains orient on the exterior ("the corona"). These microscopic "cores" can entrap hydrophobic drugs, thus providing microreservoirs for sustained drug release. Kataoka K., et al., *J. Controlled Release,* 24:119 (1993). The fundamental parameter of this supramolecular assemblage of amphiphilic polymers in aqueous solution is the Critical Micellar Concentration (CMC), which can be defined as the lowest concentration at which the dissolved macromolecules begin to self-assemble. By selection of the hydrophilic and other domains, drug delivery can be controlled and enhanced.

In one embodiment, the macromers are provided with at least one hydrophobic zone, and can form micelles including a region in which hydrophobic materials will tend to bind and thus tend to reduce escape of the drug from the formed gel. The hydrophobic zone may be enhanced by addition of materials, including polymers, which do not contribute to the formation of a gel network but which segregate into such zones to enhance their properties, such as a fatty acid, hydrocarbon, lipid, or a sterol.

The ability of the macromonomers in one embodiment to form micellar hydrophobic centers not only allows the controlled dissolution of hydrophobic bioactive compounds but also permits the hydrogel to selectively "expand" and "contract" around a transition temperature. This provides an "on-off" thermocontrol switch which permits the thermally sensitive delivery of drugs.

Figure 11:
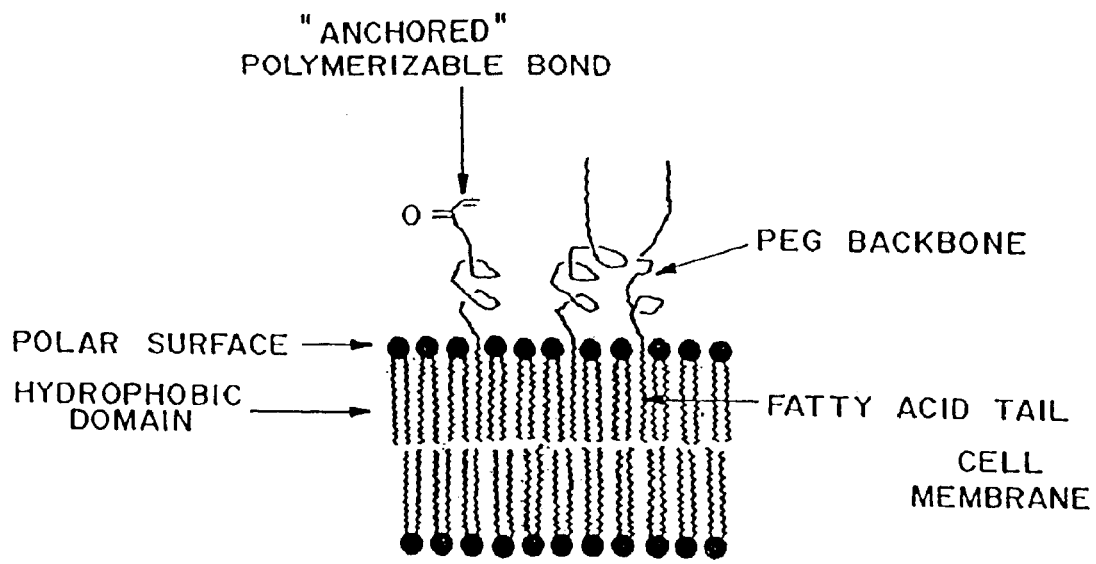
FIG. 11 is a schematic illustration of a cell membrane including hydrophobic bilayer with a macromer including a hydrophobic tail diffused into the bilayer.

The cell membrane is composed of a bilayer with the inner region being hydrophobic. This bilayer is believed to have a fluid and dynamic structure, i.e., hydrophobic molecules can move around in this structure A hydrophobic tail incorporated in a macromer can diffuse into this lipid bilayer and result in the rest of the macromonomer (thus, the hydrogel) to better adhere to the tissue surface (see FIG. 11). The choice of molecular group to be used as hydrophobic tail is guided by the fatty acid composition of the bilayer to assure minimum perturbation of the bilayer structure. Examples of suitable groups are fatty acids, diacylglycerols; molecules from membranes such as phosphatidylserine, and polycyclic hydrocarbons and derivatives, such as cholesterol, cholic acid, steroids and the like. Preferred hydrophobic groups for this purpose are normal constituents of the human body. These molecules will be used at a low concentration relative to native molecules in the membrane.

Use of macromers carrying one or more hydrophobic groups can improve the adherence of a hydrogel to a biological material by anchoring a segment of the hydrogel in the lipid bilayer. This anchoring will cause minimal perturbation to the underlying tissue because the insertion of the fatty acid terminal of the macromer into the lipid membrane involves purely physical interaction. The macromer may be applied by using a prewash of the surface with these molecules, in effect 'preparing' the surface for coupling and/or an in situ photopolymerization of a mixture of these lipid-penetrating molecules with the crosslinkable macromers.

The hydrophobic region may include oligomers of hydroxy acids such as lactic acid or glycolic acid, or oligomers of caprolactone, amino acids, anhydrides, orthoesters, phosphazenes, phosphates, polyhydroxy acids or copolymers of these subunits. Additionally the hydrophobic region may be formed of poly(propylene oxide), poly (butylene oxide), or a hydrophobic non-block mixed poly (alkylene oxide) or copolymers thereof. Biodegradable hydrophobic polyanhydrides are disclosed in, for example, U.S. Pat. Nos. 4,757,128, 4,857,311, 4,888,176, and 4,789, 724, the disclosure of which is incorporated by reference herein. Poly L-lactide, or poly D,L-lactide for example may be used. In another embodiment the hydrophobic region may be a polyester which is a copolymer of poly(lactic-co-glycolic) acid (PLGA).

The macromer also may be provided as a mixture including a hydrophobic material non-covalently associated with the macromer, wherein the hydrophobic material is, for example, a hydrocarbon, a lipid, a fatty acid, or a sterol.

Hydrophilic Regions.

Water soluble hydrophilic oligomers available in the art may be incorporated into the biodegradable macromers. The hydrophilic region can be for example, polymer blocks of poly(ethylene glycol), poly(ethylene oxide), poly(vinyl alcohol), poly(vinylpyrrolidone), poly(ethyloxazoline), or polysaccharides or carbohydrates such as hyaluronic acid, dextran, heparan sulfate, chondroitin sulfate, heparin, or alginate, or proteins such as gelatin, collagen, albumin, ovalbumin, or polyamino acids.

Biodegradable Regions

Biodegradable molecules or polymers thereof available in the art may be incorporated into the macromers. The biodegradable region is preferably hydrolyzable under in vivo conditions. In some embodiments, the different properties, such as biodegradability and hydrophobicity or hydrophilicity, may be present within the same region of the macromer.

Useful hydrolyzable groups include polymers and oligomers of glycolide, lactide, epsilon-caprolactone, other hydroxy acids, and other biologically degradable polymers that yield materials that are non-toxic or present as normal metabolites in the body. Preferred poly(alpha-hydroxy acids) are poly(glycolic acid), poly(DL-lactic acid) and poly(Ilactic acid). Other useful materials include poly(amino acids), polycarbonates, poly(anhydrides), poly(orthoesters), poly(phosphazines) and poly(phosphoesters) Polylactones such as poly(epsilon-caprolactone), poly(delta-caprolactone), poly(delta-valerolactone) and poly(gamma-butyrolactone), for example, are also useful. The biodegradable regions may have a degree of polymerization ranging from one up to values that would yield a product that was not substantially water soluble. Thus, monomeric, dimeric, trimeric, oligomeric, and polymeric regions may be used.

Biodegradable regions can be constructed from polymers or monomers using linkages susceptible to biodegradation, such as ester, peptide, anhydride, orthoester, phosphazine and phosphoester bonds. The time required for a polymer to degrade can be tailored by selecting appropriate monomers. Differences in crystallinity also alter degradation rates. For relatively hydrophobic polymers, actual mass loss only begins when the oligomeric fragments are small enough to be water soluble. Thus, initial polymer molecular weight influences the degradation rate.

Therapeutic Applications

Biodegradable, temperature responsive hydrogels can be formed in situ and may be use in a variety of therapeutic applications including surgical applications In one embodiment the gels can be applied topically to the skin to treat a variety of conditions such as abrasion, keratoses, inflammatory dermatoses, injury resulting from a surgical procedure, and disturbed keratinization. The hydrogels may include therapeutic agents such as antibiotics, or antifungals for the localized treatment of different skin conditions.

Macromers which are liquid at room temperature and gel at body temperature, such as macromers including a Pluronic™ poloxamer, may be used in treatment of burns and other external injuries. The hydrogels are useful in burn applications, since the hydrogel layer formed on the skin provides local or transdermal delivery of drug to the burn site; maintains high moisture levels on severely burned sites, thus diminishing dehydration; adheres strongly to the damaged tissue, and is elastic, thus minimizing delamination and "peeling" of the hydrogel dressing; and absorbs exudate from the wound. Hydrogels may be selected which dissolve into components which are absorbable and non-toxic, which promote healing, and gel spontaneously and quickly on the burn site, prior to optional further crosslinking.

The macromers also may be applied to biological tissue, or on the surface of a medical device, to form hydrogels in a variety of surgical applications for the treatment of tissue or organs. The gel also may be applied between two surfaces, such as tissue surfaces, to adhere the surfaces. The hydrogels may be applied to tissue such as vascular tissue, for example for the treatment of restenosis of the arteries or in angioplasty procedures. A biologically active material may be provided in the gel optionally in the form of particles, microparticles, pro-drug conjugates, or liposomes. The macromers may be designed such that the crosslinked gel changes in permneability in response to a change in temperature, ionic concentration or a change in pH, thereby altering the rate of drug release from the hydrogel.

Drug Delivery

The macromers may be crosslinked reversibly or irreversibly to form gels for controlled drug delivery applications. The composition and properties of the macromers can be selected and fabricated to produce hydrogels with desired drug delivery properties. The drug may be provided in the macromer solution prior to or after administration, and either before or after gel formation, depending on the macromer composition.

For example, the gels can be designed to have a selected rate of drug release, such as first order or zero order drug release kinetics. For specific drugs, such as peptides, the composition of the gel may be designed to result in pulsatile or mixed wave release characteristics in order to obtain maximum drug efficacy and to minimize side effects and tolerance development. Bae et at., *Pharmaceutical Research*, 8: 531 (1991).

The drug release profiles can be selected by the use of macromers and gels formed therefrom that respond to specific external stimuli such as ultrasound, temperature, pH or electric current. For example, the extent of swelling and size of these hydrogels can be modulated. Changes induced in the swelling directly correlate to the rate of release of the incorporated drugs. Through this, a particular release profile may be obtained. The hydrogels are preferably biodegradable so that removal is not required after administration or implantation.

The gels permit controlled drug delivery and release of a biologically active agent in a predictable and controlled manner locally at the targeted site where it is needed, when the tissue to be treated is localized. In other embodiments, the gels also can be used for systemic delivery.

A variety of therapeutic agents can be delivered using the hydrogels. Examples include synthetic inorganic and organic compounds, proteins and peptides, polysaccharides and other sugars, lipids, gangliosides, and nucleic acid sequences having therapeutic, prophylactic or diagnostic activities. Nucleic acid sequences include genes, antisense molecules which bind to complementary DNA to inhibit traiscription, and ribozymes. The agents to be incorporated can have a variety of biological activities, such as vasoactive agents, neuroactive agents, hormones, anticoagulants, immunomodulating agents, cytotoxic agents, antibiotics, antivirals, antisense, antigens, and antibodies. Proteins including antibodies or antigens can also be delivered. Proteins are defined as consisting of 100 amino acid residues or more; peptides are less than 100 amino acid residues. Unless otherwise stated, the term protein refers to both proteins and peptides. Examples include insulin and other hormones.

Specific materials include antibiotics, antivirals, antiinflamrnatories, both steroidal and non-steroidal, antineoplastics, antispasmodics including channel blockers, modulators of cell-extracellular matrix interactions including cell growth inhibitors and anti-adhesion molecules, enzymes and enzyme inhibitors, anticoagulants and/or antithrombotic agents, growth factors, DNA, RNA, inhibitors of DNA, RNA or protein synthesis, compounds modulating cell migration, proliferation and/or growth, vasodilating agents, and other drugs commonly used for the treatment of injury to tissue. Specific examples of these compounds include angiotensin converting enzyme inhibitors, prostacyclin, heparin, salicylates, nitrates, calcium channel blocking drugs, streptokinase, urokinase, tissue plasminogen activator (TPA) and anisoylated plasminogen activator (TPA) and anisoylated plasminogen-streptokinase activator complex (APSAC), colchicine and alkylating agents, and aptomers Specific examples of modulators of cell interactions include interleukins, platelet derived growth factor, acidic and basic fibroblast growth factor (FGF), transformation growth factor β (TGF β), epidermal growth factor (EGF), insulin-like growth factor, and antibodies thereto Specific examples of nucleic acids include genes and cDNAs encoding proteins, expression vectors, antisense and other oligonucleotides such as ribozymes which can be used to regulate or prevent gene expression. Specific examples of other bioactive agents include modified extracellular matrix components or their receptors, and lipid and cholesterol sequestrants.

Examples of proteins further include cytokines such as interferons and interleukins, poetins, and colony-stimulating factors. Carbohydrates include Sialyl Lewis$^x$ which has been shown to bind to receptors for selectins to inhibit inflammation. A "Deliverable growth factor equivalent" (abbreviated DGFE), a growth factor for a cell or tissue, may be used, which is broadly construed as including growth factors, cytokines, interferons, interleukins, proteins, colony-stimulating factors, gibberellins, auxins, and vitamins; further including peptide fragments or other active fragments of the above; and further including vectors, i.e., nucleic acid constructs capable of synthesizing such factors in the target cells, whether by transformation or transient expression; and further including effectors which stimulate or depress the synthesis of such factors in the tissue, including natural signal molecules, antisense and triplex nucleic acids, and the like. Exemplary DGFE's are vascular endothelial growth factor (VEGF), endothelial cell growth factor (ECGF), basic fibroblast growth factor (bFGF), bone morphogenetic protein (BMP), and platelet derived growth factor (PDGF), and DNA's encoding for them. Exemplary clot dissolving agents are tissue plasminogen activator, streptokinase, urokinase and heparin.

Drugs having antioxidant activity (i.e., destroying or preventing formation of active oxygen) may be provided in the hydrogel, which are useful, for example, in the prevention of adhesions. Examples include superoxide dismutase, or other protein drugs include catalases, peroxidases and general oxidases or oxidative enzymes such as cytochrome P450, glutathione peroxidase, and other native or denatured hemoproteins.

Mammalian stress response proteins or heat shock proteins, such as heat shock protein 70 (hsp 70) and hsp 90, or those stimuli which act to inhibit or reduce stress response proteins or heat shock protein expression, for example, flavonoids, may be provided in the hydrogel.

The macromers may be provided in pharmaceutical acceptable carriers known to those skilled in the art, such as saline or phosphate buffered saline. For example, suitable carriers for parenteral administration may be used.

Administration of Macromers

Modern surgical procedures which provide access to a variety of organs using minimally invasive surgical devices may be used to apply the macromers. Using techniques such as laparoscopy/endoscopy, it is possible to deposit a macromonomer solution at a localized site and subsequently polymerize it inside the body. This method of "on-site" polymerization offers unique advantages such as conformity to specific organs and adherence to underlying tissue. Hill-West J. L. et al., *Obstetrics & Gynecology*, 83:59 (1994). Catheter delivery systems available in the art also may be used as described, for example, in U.S. Pat. Nos. 5,328,471 and 5,213,580 to Slepian. The macromer also may applied during surgery conducted through the cannula of a trocar.

Formation of Microspheres

In one embodiment, the biodegrabable macromers are crosslinked, either reversibly or nonreversibly to form microspheres. As used herein, the term "microspheres" includes includes particles having a uniform spherical shape or an irregular shape, and microcapsules (having a core and an outer layer of polymer) which generally have a diameter from the nanometer range up to about 5 mm. In a preferred embodiment, the microspheres are dispersed in biocompatible, biodegradable hydrogel matrices. The microspheres are useful for controlled release and targeted delivery of drugs within the body.

The microspheres are formed in one embodiment by aggregation and subsequent polymerization of portions of the macromers which are similar in charge properties such as hydrophilicity. This results in a matrix which consists of spontaneously-assembled "nodes", which may be crosslinked covalently, and may be further covalently linked to hydrophilic bridges of the macromers to form a hydrogel.

Figure 12:
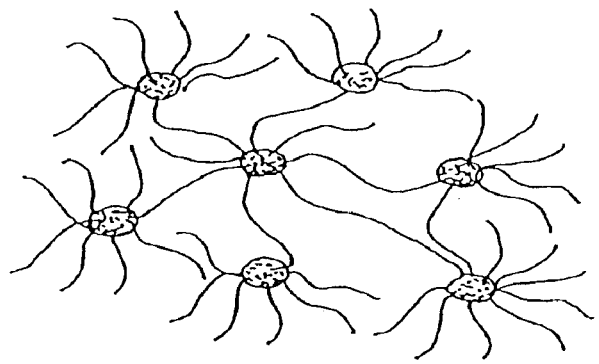
FIG. 12 is a schematic illustration of nanospheres or microspheres which can be formed by aggregation and subsequent polymerization of hydrophilic macromers.

When the macromer is amphiphilic and includes hydrophobic and hydrophilic domains, in an aqueous environment, at or above a certain concentration, the molecules to arrange themselves into organized structures called micelles, at the critical micellar concentration (CMC). These micelles can be of different shapes and sizes, though are generally spherical or elliptical shape. When the solution is water, the hydrophobic portions are at the center of the micelle while the hydrophilic tails orient themselves toward water. The interior core of a typical surfactant has a size from 10–30 Angstroms. Pluronic™ poloxamer based biodegradable macromers, as described in Example 1, undergo micellization in an aqueous environment with CMC values ranging between 0 and 5% (w/v). After photopolymerization and gelation, this micellar structure is preserved in the crosslinked gel. On a microscopic level, the gel contains micelles which are interconnected by covalent bonds to form the gel. These micellar domains or microspheres can be used for the controlled or sustained release of drugs. A schematic representation of such a material is shown in FIG. 12. Controlled, pseudo-zero order release of small compounds such as chlorohexidine is possible from such hydrogels.

The hydrogel thus is formed in one embodiment by providing a solution of macromer in aqueous solution (with or without drug); "freezing" the micellar structure of the macromer by a chemical crosslinking via a chemical reaction; adding the drug to the crosslinked macromer if it has not been already added; and using the resultant dispersed composite, containing microspheres consisting of drug-attracting micellar cores, for drug delivery.

In addition to photopolymerization, crosslinking can be implemented by, for example, isocyanate-amine chemistry, or hydroxy- or aldehyde-amine chemistry, to freeze micellar structure. For example, isocyanate terminated poloxamer lactate diol can react in water to form crosslinked polyurethane based networks. This is an advantageous method of forming a drug delivery device for local or systemic delivery, because the formation of the delivery-controlling micropheres and the microsphere-confining gel is accomplished simultaneously, and may be accomplished at the site of delivery in a few seconds by photopolymerization.

In one embodiment the macromer includes PEO segments, and hydrophobic "ends" containing reactive groups, and the micellar domains are hydrophobic and are interlinked by the PEG segments to form a hydrogel. Reversible gelling microsphere forming macromers also may be made from Pluronics™ (PEG-PPO-PEG), lactylated and acrylate-capped, which are gelled and reacted in a non-aqueous phase. A hydrophilic drug then may be added (while in the hydrophobic solvent) which partitions to the hydrophilic core. Because the micelles have been crosslinked in the hydrophobic environment, they will not be able to revert to the conformation which they would normally assume in a hydrophilic environment. The trapped hydrophilic drug molecules then need to diffuse through a relatively hydrophobic region to escape from the nanoparticle. This permits flexibility in the formation of microspheres. They may be hydrophilic or hydrophobic depending on the solvent in which they are polymerized, and on the composition of the macromers.

In other embodiments, physical or chemical crosslinking to form hydrogels (or organogels) can occur in zones other than those responsible for the primary sustained release characteristics of the matrix. For example, "single-ended" materials could have alternative reaction sites on the non-micellar ends, which could subsequently reacted to form a gel. Since matrix-controlled drug delivery is a function of both diffusion from the micelles and of matrix degradation, manipulation of the macromolecular backbone can also control matrix degradation. This can occur through stabilization of hydrolytic groups by their chemical and physical environment (for example, macromers based on reverse Pluronic™ gels are more stable than normal Pluronic™ gels, in aqueous solution). It is possible that the increased hydrophobicity of the environment of the lactide ester bonds, due to the adjacent block being PPO rather than PEO, inhibits hydrolysis of the bond.

Alternatively, and particularly in gel-forming compositions, the cross-linking reactive groups or biodegradable groups may be in the hydrophilic portions of the macromers, so that the hydrophobic domains would not be locally crosslinked in the hydrophobic regions, while the micelles would still be stabilized by the crosslinking of the material, and particular hydrophobic sections of macromers would be sterically restricted to one or only a few different micelles. In either of these cases, the hydrophobic zones are not rigidly crosslinked, but are connected to crosslinks via the hydrophilic blocks, which may be very flexible. The hydrophobic blocks thus can associate above or below a critical temperature, and dissociate on change in temperature. This allows, for example, both thermosensitive gelation and thermosensitive variation in drug diffusion rate.

The hydrogels may be designed to be biodegradable by incorporation of a group such as a lactide, glycolide or other self-degrading linkage. Alternatively, this is not necessary when non-gelled nanospheres are formed, since these are small enough to be removed by phagocytosis. Control of the rates of delivery of both small and large molecules can be obtained by control of the hydrophobicity of the associating hydrophobic domains of amphipathic hydrogels.

The crosslinked microspheres containing a biologically active agent, in either gel or dispersion form, can be made in a single step. In addition to drug delivery applications, the method is suitable for non-medical uses including delivery of agricultural materials such as herbicides and pesticides and in water treatment.

The present invention will be further understood by reference to the following non-limiting examples.

EXAMPLE 1

Synthesis and Thermal Responsiveness of F127-(Lactate)6Acrylate a) Synthesis.

F127-(lactate)O-acrylate (unlactated control) (=F127A2?) was synthesized by acrylating 100 g of Pluronic™ F127 (polypropylene oxide-polyethylene oxide block copolymer, BASF, mol. wt. 12000) ("F127") in anhydrous toluene using triethylamine and acryloyl chloride, in an argon atmosphere at 60° C. for 10 minutes. The hot, turbid reaction mixture was filtered and the filtrate was added to a large excess of hexane. The monomer was collected by vacuum filtration and dried in vacuum to a constant weight.

F127-(lactate)6-acrylate was synthesized as follows. F127 was melt dried in vacuo at 100° C. for 4 hours. D,L-lactide (Boehringer Ingelheim) was added to the melt under a nitrogen flush, followed by stannous octoate as a ring opening catalyst. After a reaction time of 4 hours, the melt was dissolved in toluene and precipitated in a large excess of hexane. Acrylation of F127-(lactate)6 was carried out as described above for the acrylation of F127-(lactate) O-acrylate. All macromonomers were characterized by NMR and HPLC.

The relationship between the macromer, the thermally-reversible (physical) gel, and the irreversible (crosslinked) gel is shown in FIG. 1.

b) Measurement of the Sol-Gel Transition as a Function of Concentration and Temperature.

Thermoreversible gel formation of the aqueous solutions of the macromonomers at a certain transition temperature was demonstrated. This transition temperature was recorded as a function of temperature and concentration. The results demonstrated that sol-gel transition can be controlled through the incorporation of hydrophobic lactyl units.

Transition temperature as a function of concentration was determined by preparing 20% w/v aqueous solutions of F127-(lactate)O-acrylate and F127-(lactate)6-acrylate as stock solutions. 15% (w/v), 12.5% (w/v), 10% (w/v) and 5% (w/v) macromonomer aqueous? solutions in screw cap vials were prepared by dilutions of the stock solutions. The solutions were allowed to equilibrate at 25° C. The vials were inverted and observed for fluid flow. The concentration at which no fluid flow was observed was recorded (see Table 1).

The transition temperature as a function of temperature was determined by preparing 10% (w/v) aqueous solutions of F127-(lactate)6-acrylate and F127-(lactate)O-acrylate and equilibrating them at room temperature. (The concentration of the solutions are wt/vol % in aqueous solution unless otherwise stated.) The sample vials were immersed in a temperature controlled bath and the fluid flow was observed at different temperatures. The temperature at which no fluid flow was observed was recorded (see Table 1).

TABLE 1

| Macromonomers | Sol-Gel Transition (% w/v)** | Sol-Gel Transition (° C.)*** |
|---|---|---|
| F127-(Lactate)0-Acrylate | 30 | 40 |
| F127-(Lactate)6-Acrylate | 10 | 25 |

**Sol-Gel Transition as a function of concentration (temperature 25° C.).
***Sol-Gel Transition of 10% w/v solutions as a function of temperature.

c) Polymerization and Measurement of Hydrogel Dimensions.

Figure 2:
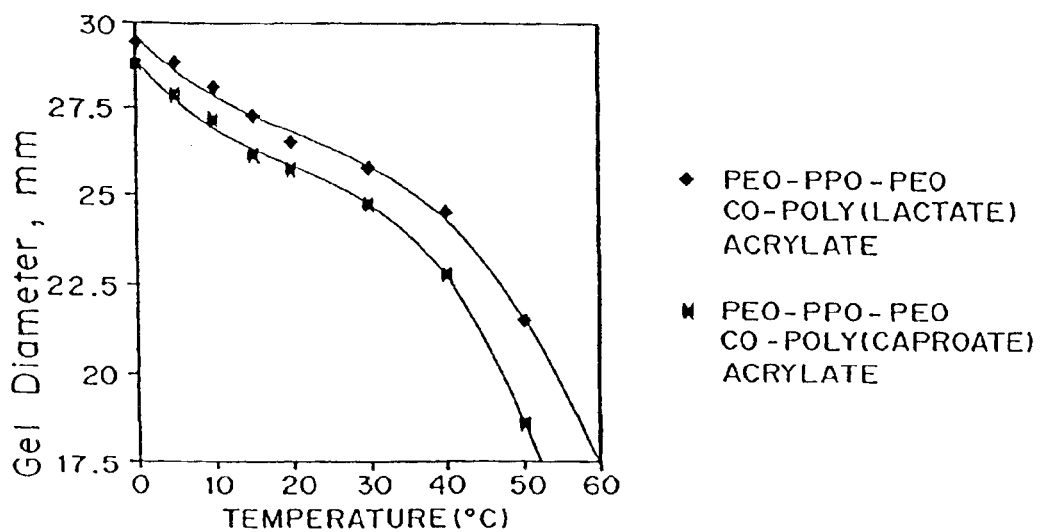
FIG. 2 is a graph of temperature-dependent changes in gel volume of gels formed by photopolymerization of an acrylated polypropylene oxide-polyethylene oxide block copolymer containing a biodegradable region.

A 10% solution of F127-(lactate)6-acrylate in PBS (phosphate buffered saline) was polymerized using long wave UV light. The polymerizations were performed in a cylindrical plastic mold. Darocur™ 2959 (Ciba Geigy) was used as the photoinitiator. The hydrogel was allowed to reach equilibrium swelling by immersing in PBS for 24 hours at ambient temperature. The change in dimension of the hydrogel at temperatures ranging from 0–50° C. was measured using vernier calipers, and is shown in FIG. 2. At low temperatures, the hydrophobic PPO (polypropylene oxide) segments of the hydrogel may dissolve and swell, and increase the dimensions of the gel. At high temperatures, the PPO segments may become hydrophobic and collapse into micromicellar hydrophobic domains, which exclude water resulting in reduced swelling and smaller dimensions.

d) Degradation Experiments.

Hydrogels were prepared using 10% macromonomer solution as mentioned before and the degradation of hydrogel was monitored gravimetrically at various intervals of time. The experiments were performed at 37° C. in PBS. The lactate based photopolymerized hydrogel completely degraded in 22 days (at 37° C., in PBS).

Thus, the macromers can be photopolymerized to form thermoresponsive hydrogels which degrade under physiological conditions.

EXAMPLE 2

Dextran Release by F127A2

Figure 3:
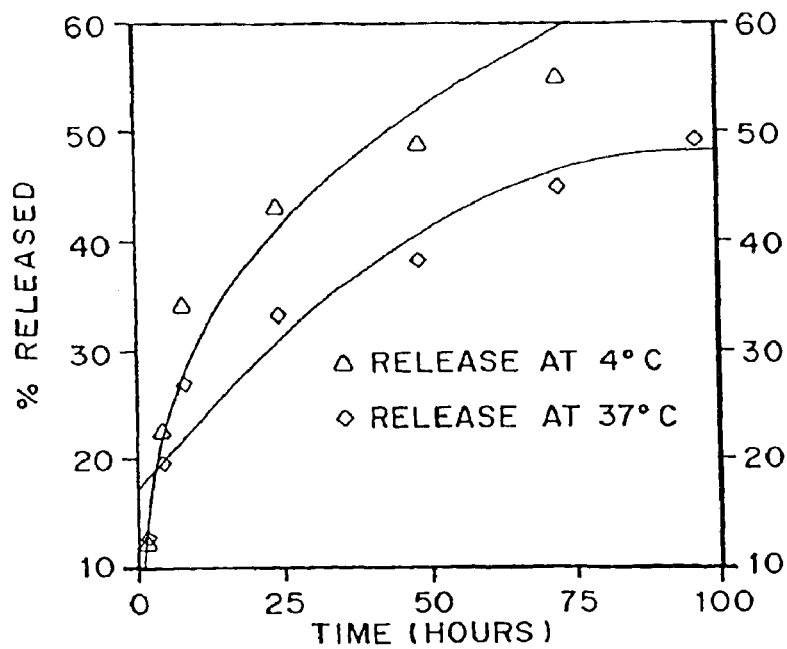
FIG. 3 is a graph showing the effects of temperature on dextran release from a gel formed by photopolymerization of an acrylated polypropylene oxide-polyethylene oxide block copolymer.

The non-degradable material, F127A2, was made as described above in Example 1, with no addition of hydroxy acid to the Pluronic™ polymer backbone. Dextran (labeled with fluorescein) of molecular weight 71,000 daltons was mixed at 1% final concentration with F127A2 macromer (final concentration 10% wt/vol, in water) and polymerized as described in Example 1. Release of dextran was determined by visible absorbance. Release kinetics were significantly altered by temperature, as shown in FIG. 3.

EXAMPLE 3

Synthesis of Macromers with Biodegradable Linking Groups

Four monomer types were made by the general procedures described in Example 1, each containing about 4 units of each of four different biodegradable linkers, designated by L (lactate), C (caprolactone), G (glycolide), and TMC (trimethylene carbonate). Parameters for the synthesis of the thermnosensitive macromonomers are listed in Table 2. Properties of the monomers characterized are listed in Table 3, including biodegradable segment and end group incorporation by HPLC and NMR, and Mn determined by GPC and NMR.

TABLE 2

| Compound | M.W. (g/mole) | PPO M.W. | PEO M.W. | Feed Ratio Monomer/diol | Temp ° C./time (h) | Yield (g) |
|---|---|---|---|---|---|---|
| F127L4A2 | 12600 | 3780 | 8820 | 4 | 180–190/5 | 80.46 |
| F127C4A2 | 12600 | 3780 | 8820 | 4 | 180–190/5 | 81.38 |
| F127G4A2 | 12600 | 3780 | 8820 | 4 | 180–190/5 | 71.89 |
| F127TMC4A2 | 12600 | 3780 | 8820 | 4 | 180–190/5 | 79.29 |

TABLE 3

| Macromonomer | Biodeg. Seg. Incorp. (HPLC) | Biodeg. Seg. Incorp. (MNR) | End Group Incorp. (HPLC) | End Group Incorp. (NMR) | Mn GPC g/mol | Mn NMR g/mol | Mn Expected g/mol |
|---|---|---|---|---|---|---|---|
| F127L4A2 | 5.68 ± 0.01 | 5.58 | 2.09 ± 0.01 | 2.00 | 10800 | 11316 | 12998 |
| F127G4A2 | 5.39 ± 0.02 | 5.04 | 2.05 ± 0.02 | 2.31 | 10800 | 10804 | 12942 |
| F127C4A2 | 5.49 ± 0.02 | 5.45 | 2.09 ± 0.03 | 2.11 | 10000 | 13062 | 13166 |
| F127TMC4A2 | — | 3.26 | 2.08 ± 0.03 | 2.09 | 12100 | NA | — |

The macromers and related prior art materials are referred to herein in the form XXXLLAA, where XXX is either part of the trade name of a precursor polymer (e.g., L81 for Pluronic™ L81 poloxamer) or refers to another property of the base polymer (e.g., 8K for 8,000 nominal Dalton PEO). LL denotes the terminal block, typically of a degradable hydroxy acid (e.g., L5 denotes an average of 5 lactate residues per arm of the polymer), where L, G, C and TMC or T represent, respectively, lactate, glycolate, epsilon-caproate, and trimethylenecarbonate. AA represents a terminal group; for example, A is for acrylate, so A2 would represent 2 acrylate terminations on the macromer as a whole.

Figure 4:
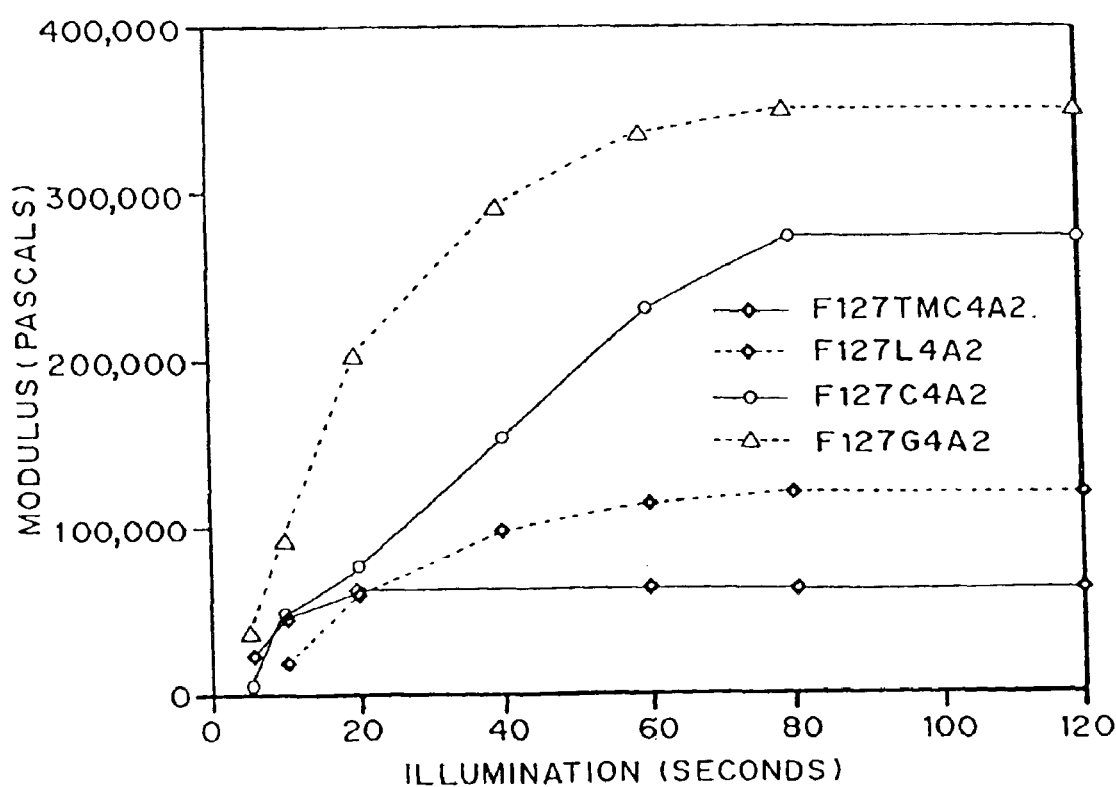
FIG. 4 is a graph illustrating the variation in the speed of photocrosslinking of acrylated polypropylene oxide-polyethylene oxide block copolymers having incorporated therein different biodegradable regions.
Figure 5:
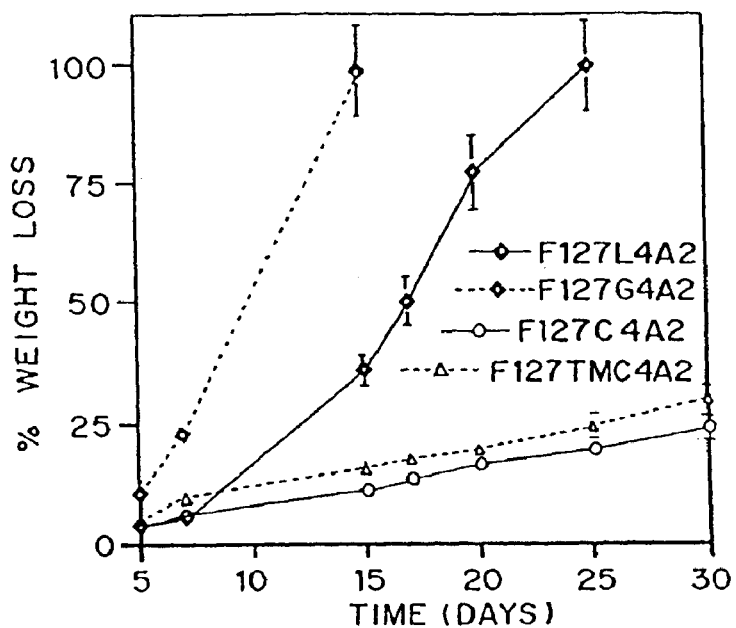
FIG. 5 is a graph showing the in vitro profiles of degradation rate of gels formed by photocrosslinking of acrylated polypropylene oxide-polyethylene oxide block copolymers having incorporated therein different biodegradable regions.

The monomers differed in their rate of polymerization and rate of degradation. The long UV photopolymerization profiles are shown in FIG. 4. The in vitro degradation profiles of the crosslinked hydrogels are shown in FIG. 5.

Figure 6:
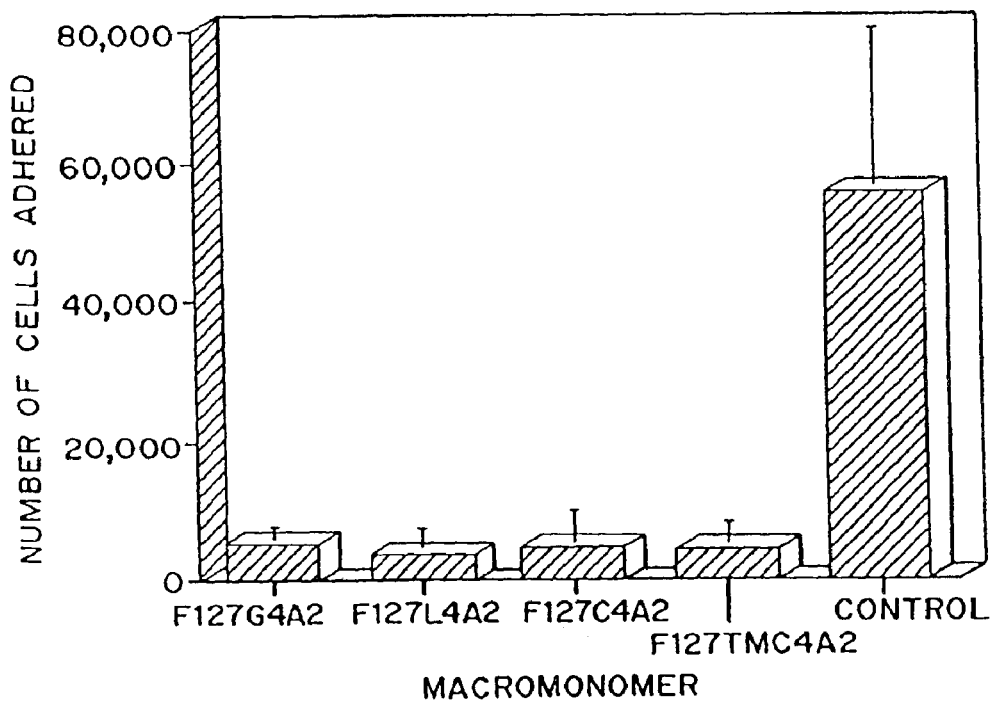
FIG. 6 is a graph illustrating the biocompatibility of gels formed by photocrosslinking acrylated polypropylene oxide-polyethylene oxide block copolymers having incorporated therein different biodegradable regions.
Figure 7A:
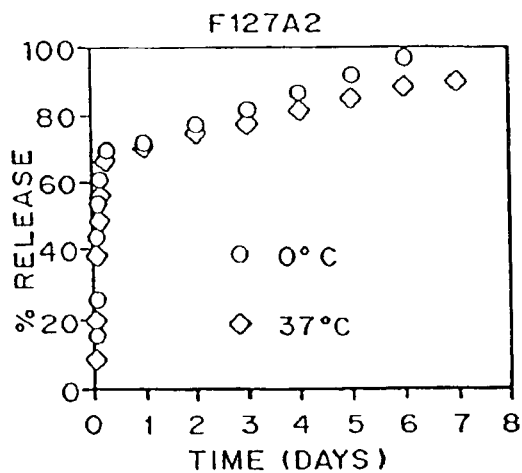
FIGS. 7a, 7b, 7c, and 7d show graphs illustrating release of fluorescent dextran from gels formed by photocrosslinking acrylated polypropylene oxide-polyethylene oxide block copolymers having incorporated therein biodegradable linkers.
Figure 7B:
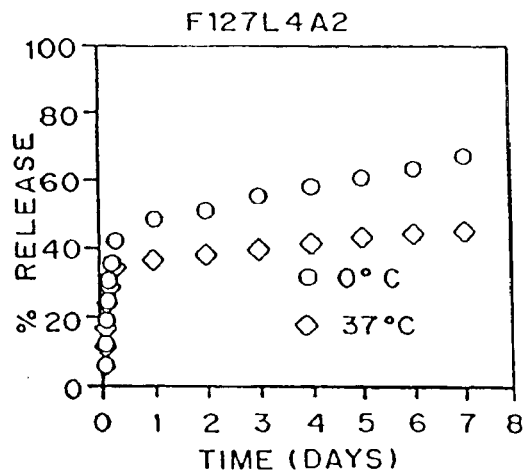
Figure 7C:
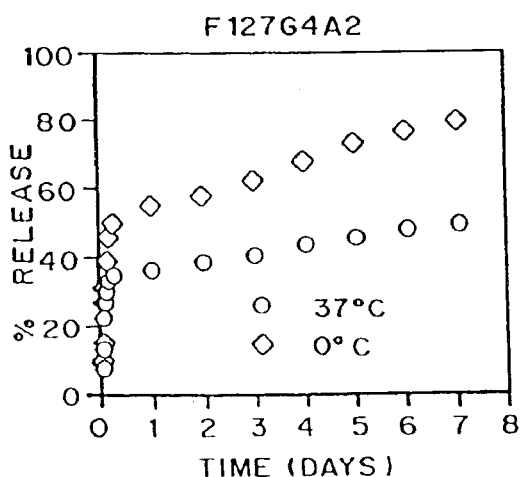
Figure 7D:
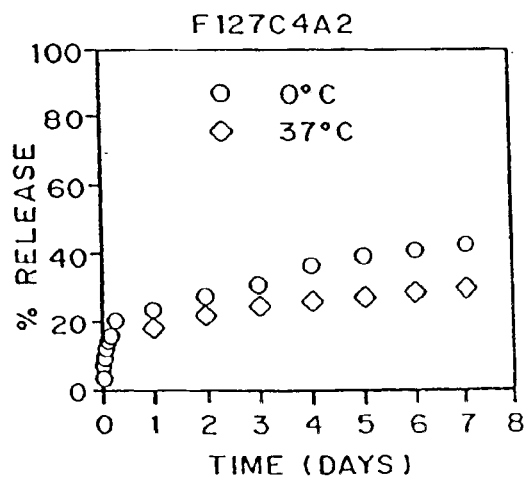
Figure 8A:
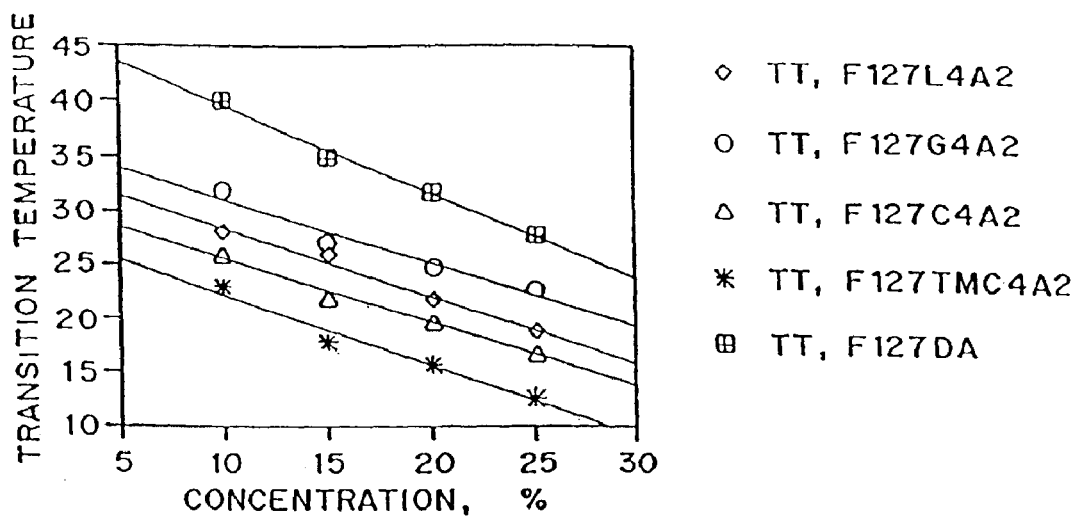
FIGS. 8a and 8b show graphs of transition temperatures of gels formed from macromers containing biodegradable linkers.
Figure 8B:
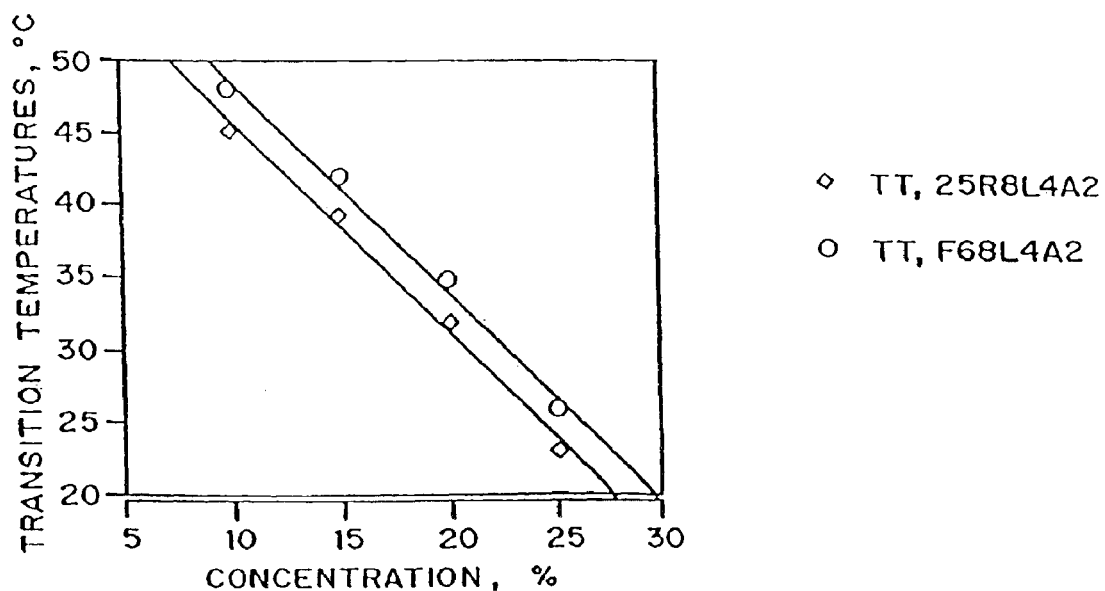

The macromers had similar biocompatibility profiles, as shown in FIG. 6, as measured by the HFF cell adhesion test. In FIGS. 7a, 7b, 7c, and 7d, release rates of fluorescent dextran at 37° C. and 0° C. are shown for a prior art material (F127A2) and for macromers with degradable hydrophobic blocks formed of lactide (F127L4A2), glycolide (F127G4A2) and caprolactone (F127C4A2). A longer period of quasi-zero order delivery, after the initial burst, and a distinct difference in the rates of efflux between the lower and higher temperatures, is obtained with the macromers including the degradable blocks, in comparison to the prior art material. In FIGS. 8a and 8b, the transition temperatures (for volume change and change of dextran release rate) are shown as a function of macromer concentration in the gel for the above materials and also a trimethylene carbonate based material (F127TMC4A2), a "reverse" meroxapol material with lactide (25R8L4A2), and a "normal" material (F68L4A2) of equivalent hydrophobicity The HFF test was conducted as follows:
a.) Preparation of Gel.

0.5 gram of test material was dissolved in 4–5 ml standard reconstitution solution (Irgacure 1200 ppm, 3% Pluronic F127). The solution was filter sterilized using 0.2 micron filter. In a sterile hood, a glass coverslip (18 mm sq) was sterilized using 70% ethanol and was placed in a 6 well, 35 mm tissue culture dish. 200 µL of the sterile macromonomer solution was spread on a sterile coverslip. The solution was then exposed to long wavelength UV light (Black Ray, 20 mW/cm2, 1 minute) to form a gel.

c) Preparation of Cell Suspension.

Human foreskin fibroblasts (HFF) cells were purchased from ATCC. Cells were used at a passage 22–23. HFF cells were cultured in a standard tissue culture ware in a humidified atmosphere containing 5% $CO_2$. Cells were detached from the culture flask using a 3 ml trypsin/EDTA solution (0.05%/0.53 mm) and centrifuged (2500 rpm, 3 minutes). The cell pilot was resuspended in cell culture medium (DMEM+10% FCS) at a concentration of 250000 cells/ml.

d) Cell Attachment Assay.

The gels were washed with 3 ml DMEM (Dulbecco's Modified Eagles' Medium) solution and then seeded with 25000 cells/cm2 cell density. After 18 h, the gel surface and tissue culture polystyrene surface were observed under microscope and photographed. The gels were separated from coverslip and transferred into a new petri dish. The cells adhered to the gels were detached using 3 ml trypsin/EDTA (0.05%/0.53 mm) solution. A Coulter counter was used to determine the cell density.

EXAMPLE 4

Effects of Linking Group Hydrophobicity on Small Molecule Delivery

Figure 9:
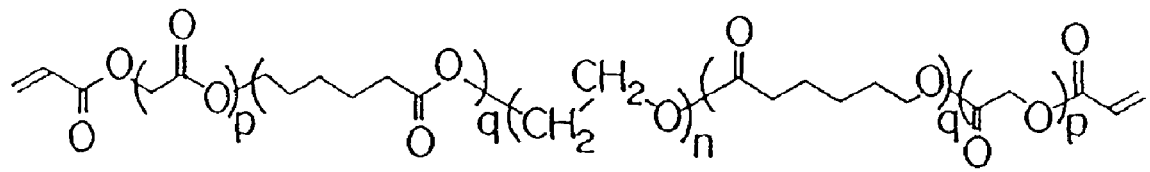
FIG. 9 illustrates the chemical structures of biodegradable crosslinkable macromers consisting of acrylated poly(propylene oxide)-poly(ethylene oxide) block copolymers having incorporated therein a biodegradable linker.

Micelle-forming biodegradable macromers were synthesized and characterized which included a non-thermosensitive core. The macromers illustrated the effects of hydrophobicity on delivery capacity for small hydrophobic molecules. The macromers were formed by synthesizing copolymers of PEG (molecular weight 8000) with different combinations of polycaprolactone and polyglycolate which were then end capped with acrylate moieties. The structures are shown in FIG. 9, where p is the number of glycolic acid groups and q is the number of caprolactone groups. Hydrophobicity of the mixed hydroxy acid blocks increases from A to D. The ability of these monomers to solubilize model hydrophobic drugs was demonstrated by a study of the CMC through the gradual dissolution of a molecular probe, 1,6 diphenyl 1,3,5-hexatriene (DPH). effect of hydrophobicity on drug incorporation into gels a) Synthesis of Monomers.

The molecular structures of the monomers are shown in FIG. 9. Polyethylene glycol 8000 (Union Carbide) was melt-dried at 100–110° C. in vacuum (10–15 mm Hg) for 4–6 hours. Caprolactone (predistilled, Aldrich), and glycolide, were charged at appropriate ratios into a Schlenk-type reaction vessel and stannous 2-ethyl hexanoate (Sigma) was added as a ring opening catalyst. The reaction was carried out for 4 hours in an inert atmosphere at 180° C. The reaction mixture was then cooled to 80° C., dissolved in toluene, precipitated in hexane and the product was collected by vacuum filtration. The product was redissolved in toluene and dried by azeotropic distillation.

Acrylation was carried out by the dropwise addition of a 2 molar excess of acryloyl chloride and triethylamine under a nitrogen flush at 65° C. for 1 hour. By-product salts were removed by vacuum filtration. The product was isolated by precipitation in a large excess of hexane followed by vacuum filtration. The monomers were characterized by NMR on a Varian 300 MHz nuclear magnetic spectrometer.

b) Determination of Critical Micellar Concentrations.

The hydrophobic dye 1,6, diphenyl 1,3,5-hexatriene (Aldrich), (DPH), which demonstrates enhanced absorbance (356 mn) at the CMC due to associative interactions, was used in this study. Alexandridis et al., *Macromolecules*, 27:2414 (1994). A stock solution of DPH was prepared in methanol (0.4 mM). Aqueous monomer solutions were prepared by dissolution in PBS and dilution to the desired concentrations. 10 µl of the dye solution were added to each vial with equilibration for at least 1 hour. The absorption spectra of the polymer/dye/water solutions were recorded in the 250–500 nm range using a Hitachi UV-VIS Spectrometer.

c) Photopolymerization.

Photopolymerization of the polymer solutions were carried out in both visible and ultraviolet light systems as described in: Sawhney A. S. et al., *Macromolecules*, 26: 581 (1993); and PCT WO 93/17669 by Hubbell J. A. et al.

d) In vitro Degradation.

200 µl of 10% monomer solution were UV polymerized to form a gel. The degradation of the hydrogels was monitored at 37° C. in PBS.

e) Results

Figure 10:
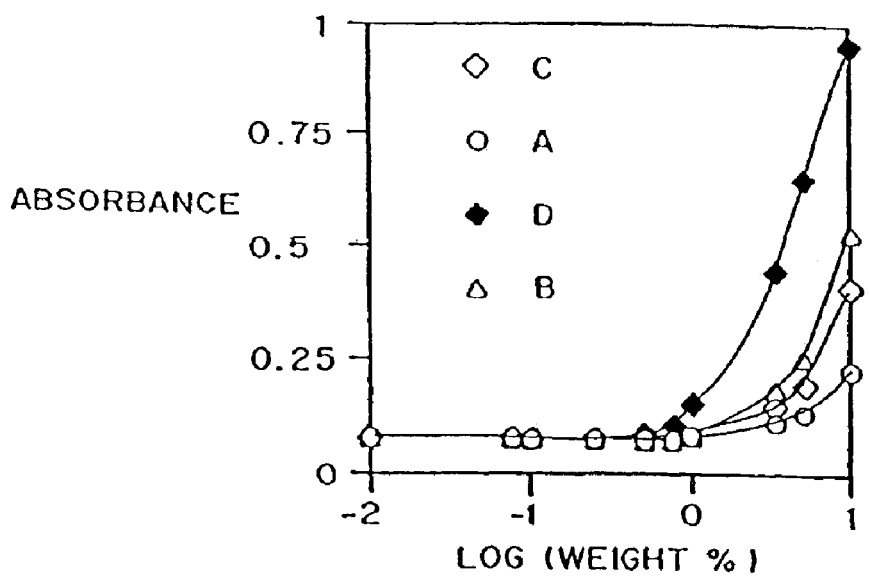
FIG. 10 is a graph of absorbance of a hydrophobic dye vs. log (weight %) of solutions of biodegradable macromers having a hydrophobic region incorporated therein.

In the synthesis, hydrophobic segments of the monomers were changed by using various combinations of caproate and glycolate linkages in the molecule. The critical micellization point was obtained from the first inflection of the absorption vs. concentration curve. The curves are shown in FIG. 10. It is evident from the curves that the solubility of the dye is enhanced with increasing concentration of the monomer. The CMC values during aggregation and photopolymerization for various monomers are listed in Table 4.

TABLE 4

| Monomer | Critical Micellar Concentration (%) | Gel* Time Initiated Using UV Light (secs) | Gel** Time Initiated Using Visible Light (secs) | Total Degradation time (days) |
|---|---|---|---|---|
| A | 0.92 | 5.5 ± 0.4 | 8.9 ± 0.1 | 10 |
| B | 0.55 | 5.8 ± 0.1 | 8.2 ± 0.5 | 14 |
| C | 0.32 | 5.2 ± 0.2 | 9.8 ± 0.4 | 16 |
| D | 0.28 | 4.6 ± 0.1 | 10.4 ± 0.3 | 44 |

*2,2-Dimethoxy-2-phenylacetophenone as UV initiator, Long UV light, 20% monomer conc.
**Eosin, triethanolamine initiating system; green light source, 20% monomer conc.

The CMC value is lowered with increase in caproate content of the monomer. This may be due to the tighter aggregation of the hydrophobic caproate moieties. The fast gelling ability of these monomers under UV and visible light is illustrated in Table 4. The gel times range between 4–12 seconds. The photopolymerized hydrogels degrade under aqueous conditions. The degradation times, i.e., times to substantially complete dissolution, varied from 10–44 days, increasing with cap/gly ratio. The fast gelation times of these monomers, their ability to dissolve hydrophobic solutes and their controlled degradation rates render them excellent candidates for localized drug delivery.

EXAMPLE 5

Synthesis of Macromers Forming Liquid Crystal Phases a) Synthesis of Macromers.

P105L4A2, P84L5A2 and T904L5A2 macromers were synthesized by standard procedures, generally as described in Example 1, from commercial base polymers (P105 Pluronic™ poloxamer; T904 Tetronic four-armed ionic-group containing polaxamer; P84 Pluronic™ reverse poloxamer, or meroxapol).

b) Characterization of Optical Effects and Drug Release Properties.

Aqueous solutions were prepared, and observed for anomalous optical effects ("Schlieren") without crosslinking. Rates of release of a drug were observed, wherein the drug had a molecular weight about 500 D, and substantial water solubility, as well as a hydrophobic region.

Aqueous solutions of all three macromers formed "Schlieren" type liquid crystalline phases at concentrations of 55% and higher, at room temperatures. A temperature study of the LC phases showed that the LC phases for P84L4A2 and T904L4A2 are not stable at temperatures higher than 30–35° C. The LC phase for these two polymers phase separates into two phases at T>35° C., one being an isotropic polymeric phase that is not transparent to light and another phase that seemed to consist of water. In contrast, a concentrated solution of P105L4A2 (75%w/v) displays a highly anisotropic LC phase that maintains its stability to temperatures up to 110° C.

Aqueous solutions of P105L4A2 (in high concentrations) formed a highly anisotropic liquid crystalline phase (LC phase) that results in good drug entrapment to slow down release It was also observed that P84L5A2 and T904L5A2 had significant differences in the self-assembling characteristics (LC). It is possible that the drug is entrapped in the stable, highly oriented LC Phase of a p105L4A2/water system. P84L4A2 and T904L4A2 form LC phases with water, but these phases are not stable above 30–35° C. At higher temperatures, the drug as well as some of the water are excluded from the polymeric domains.

EXAMPLE 6

Treatment of Burns

The pluronic poloxamer based macromonomers, such as F127-TMC acrylate, have a "paste-like" consistency at temperatures above 37° C., and have flow characteristics at low temperatures. A "cool" formulated solution, optionally containing an appropriate drug (such as an antibiotic) is poured on a burn site, providing instant relief. At body temperatures, the formulation gels to a paste like consistency. The gel is then crosslinked, preferably by the action of light on an included photoinitiator. The characterization of photopolymerized hydrogels as carriers for therapeutic materials to influence wound healing is described in Sawhney et al., "The 21st Annual Meeting of the Society for Biomaterials," Mar. 18–22, 1995, San Francisco, Calif., Abstract, the disclosure of which is incorporated herein by reference.

The hydrogel layer on the skin provides transdermal delivery of drug to the burn site; maintains high moisture levels on severely burned sites, thus preventing dehydration; adheres strongly to the damaged tissue, and is elastic, thus preventing delamination and "peeling" of the hydrogel dressing; and absorbs exudate from the wound. After a suitable time, controlled by the nature of the lining group (trimethylene carbonate in this example, giving a residence time of over a week), the gel will dissolve into components which are absorbable or innocuous. It has been demonstrated in other experiments that related gel formulations, based on a polyethyleneglycol backbone such as the material 8KL5A2 (i.e,. PEO of molecular weight 8,000, with 5 lactate groups on each end terminated with acrylate groups), do not retard the healing of full thickness biopsy wounds in rat skin. The pentablock polymer F127-TMC acrylate of Example 3 is improved in comparison to the prior-art 8KL5A2 polyethylene glycol-based triblock formula in that it gels spontaneously on the burn site, and thus does not tend to run off the site before it can be photocrosslinked.

EXAMPLE 7

Use of Hydrophobic Macromers to Increase Tissue Adherence

Use of macromers carrying one or more hydrophobic groups can improve the adherence of a hydrogel to a biological material. A macromer having having this property was synthesised. The base polymer was a Tetronic™ 4-armed polymer based on ethylene diamine, where each arm is a PEG-PPO-PEG triblock copolymer. The base polymer was extended with lactide as previously described in Example 1, and then capped with about two moles of palmitoyl chloride per mole of polymer, in order to cap about half of the arms. The remainder of the hydroxyls were capped with acroyl chloride, as described in Example 1. The resulting macromer was dispersed in water and was polymerized in contact with tissue, to which it adhered tenaciously.

EXAMPLE 8

Formation of Microspheres

Pluronic™ based biodegradable macromers made as described above above, such as the materials of Example 3, in an aqueous solution formed micelles with a CMC value ranging from about 1% to 5% w/v. After photopolymerization, the structure of the micelle is substantially preserved.

EXAMPLE 9

Synthesis of F127-Dimer Isocyanate-F127 Lactate Acrylate

Two molecules of a macromer diol (Pluronic F127) are coupled with one molecule of a dilsocyanate (dimer isocyanate) to produce higher di- and tri-functional alcohols, to provide macromers with high elasticity, high distensibility and high tissue adherence.

The following reagents are used: Pluronic F127 (BASF lot # WPM N 581B, Mn=12200); dimer isocyanate (DDI-1410, Henkel Lot# HL 20037, % NCO=14.1%); and dibutyltin dilaurate.

Synthesis of F127-DDI-F127: 366 g of Pluronic F127 was heated to 100° C. under vacuum for four hours to produce a melt. DDI-1410 (8.94 g) and dibutyltin dilaurate (0.115 g) was added to the melt (melt temperature 70° C.) and stirred vigorously for 4 hours. The mixture readily crystallized when cooled. Product was a white waxy crystalline material. Theoretical molecular weight=24,996 Daltons.

Synthesis of F127-DDI-F127 Lactate, diol: 100 g of F127-DDI-F127 was dried for 4 hours under vacuum at 100° C. 4.67 g of (D,L) Lactide was charged to the reaction pot under an argon flush. Stannous 2-ethyl hexanoate (0.5 mole percent) was added to the reaction. The melt was vigorously stirred at 150° C. under argon for 4 hours. The product was isolated by precipitation in hexane, followed by filtration. The product was a white, crystalline, flaky material.

Synthesis of F127-DDI-F127 Lactate$_5$ acrylate: 100 g of F127-DDI-F127 Lactates diol was charged into a 1000 ml three-necked reaction vessel. 800 ml of toluene (Aldrich, 0.005% water content) was added to the flask. 50–75 ml of toluene was azeotroped off to ensure moisture free reactants. 2.427 ml of predistilled triethylamine, followed by 2.165 ml of acryloyl chloride was added to the reaction mixture at 65° C. After one hour of reaction time, the turbid reaction mixture was filtered, and isolated into a white powder by precipitation into a large excess of hexane. The product was collected by vacuum filtration and dried to a constant weight.

Molecular structure determination was carried out by NMR, IR. The product was found to be soluble in water and crosslinkable by visible and UV light. Percent water uptake of fully cured 10% w/w hydrogels=22.1%. Hydrogels formed by photopolymerization at 10% concentration while on dead bovine tissue were determined to be generally well adherent.

P105-DDI-P105 lactate acrylate and L81-DDI-L81 lactate acrylate was synthesized from the respective Pluronic poloxamer starting materials (P105,L81) by the procedure described above. These macromers were insoluble in water. They were used to encapsulate bioactive molecules in hydrophobic matrices to achieve sustained drug release.

EXAMPLE 10

Synthesis of F127-DDI-F127 Isophorone Isocyanate

The synthesis and polymerization of a macromer which crosslinks without involving free radical polymerization is demonstrated. 50 g of F127-DDI-F127 diol, prepared as in Example 9, was dissolved in 100 ml of toluene in a three necked reaction flask. 90 ml of toluene was distilled off azeotropically at 110° C. under argon. The flask was maintained at 100° C. for 12 hours under vacuum (12 mm Hg). The reaction flask was then cooled to room temp, and 200 ml of dry methylene chloride was added to the reaction flask. 0.445 g of isophorone isocyanate (Aldrich) was added (in a bolus) to the reaction flask at approximately 30° C. 0.15 g of dibutyltin laurate was added to the reaction mixture. The reaction mixture was stirred under argon at 30° C. for 12 hours, and precipitated in 1000 ml of hexane (EM Sciences). White flakes were collected by vacuum filtration, and rinsed with 150 ml of hexane. The product was dried in a vacuum oven to a constant weight. Characterization by NMR, IR showed synthesis of the expected material.

The polymerizability of F127-DDI-F127 isophorone isocyanate was evaluated. Partially dried product (0.16 g) was added to 1.44 g of deionized water. The product initially formed bubbles in contact with water, then dissolved over approximately 3 days to form a viscous solution. To test polymerizability, 200 mg of F127-DDI-F127 isophorone isocyanate solution of polyethyleneimine in methylene chloride. The solution was stirred vigorously for a few seconds. A gelatineous product was observed. Gel time: 5.9 seconds. Polyethyleneimine is believed to have hemostatic properties; this formulation thus is potentially suitable for a topical wound dressing. In addition, structures formed of these materials can be used as drug depots.

EXAMPLE 11

Effect of Hydrophobicity on Drug Release Kinetics for Bulk Devices

Figure 13:
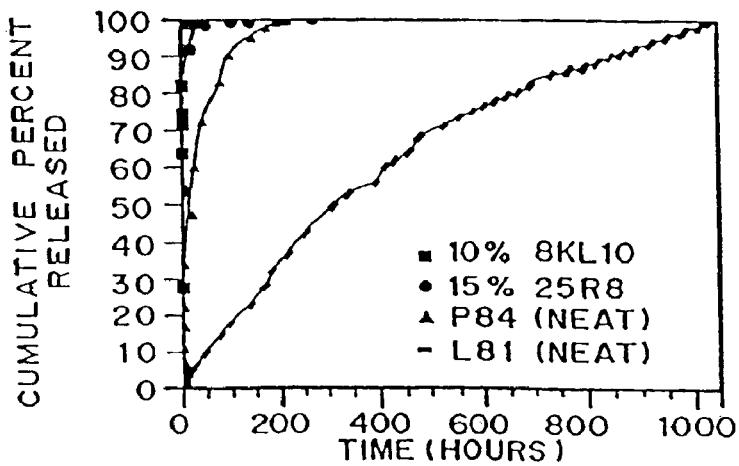
FIG. 13 is a graph which shows the rate of release of a small drug from gels formed from hydrophobic macromers.

Macromers were synthesized having a wide range of hydrophobicities ranging from 0–90% PPO content. All macromers were tested at 15% macromer concentration except those whose PPO content was greater than 60% which were used neat. FIG. 13 shows the rate of release of a small drug from gels of these macromers. At 10 and 15% macromer loading (8KL10, prior art; 25R8L4A2, based on a "reverse" Pluronic polymer) and PPO content of less than 60% hydrophobic partitioning did not show a significant effect on prolonging 500 Da sparingly soluble drug release. Devices prepared with neat macromers (PPO content>60%; P84 L5A2 and L81L5A2, synthesized by general procedures as described above) showed a significant ability of these highly hydrophobic, dense macromers to retard water permeation and drug dissolution In the extreme case (L81L5A2; PPO content=90%), the release kinetics showed first order release with half of the drug being released from the device over 17 days with the remainder being eluted from the device over a total of 66 days.

EXAMPLE 12

Effect of Polymer Hydrophobicity on Drug Diffusivity

Figure 14:
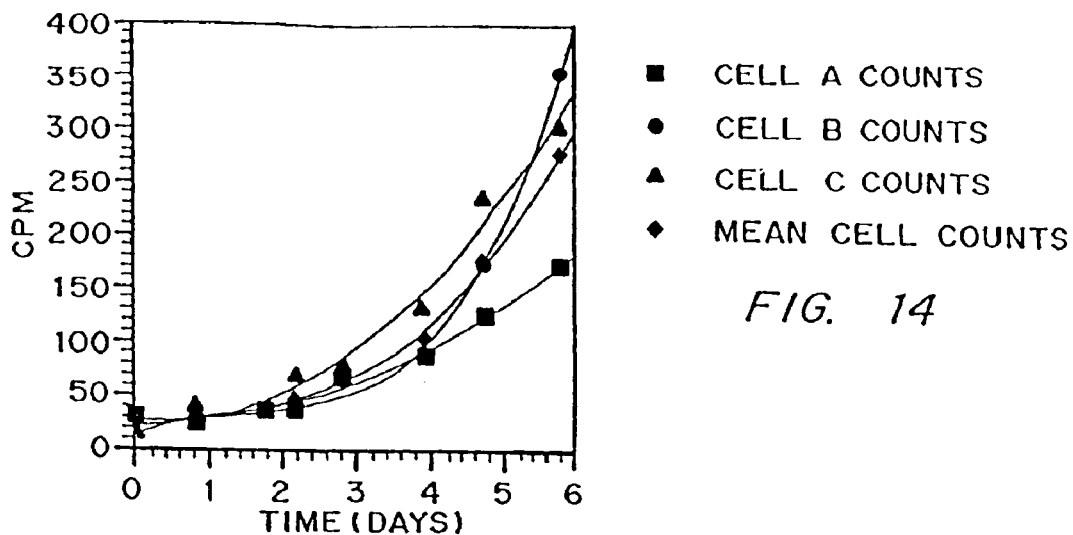
FIGS. 14 and 15 are graphs showing diffusivity of a sparingly water soluble drug through a hydrophobic hydrogel.
Figure 15:
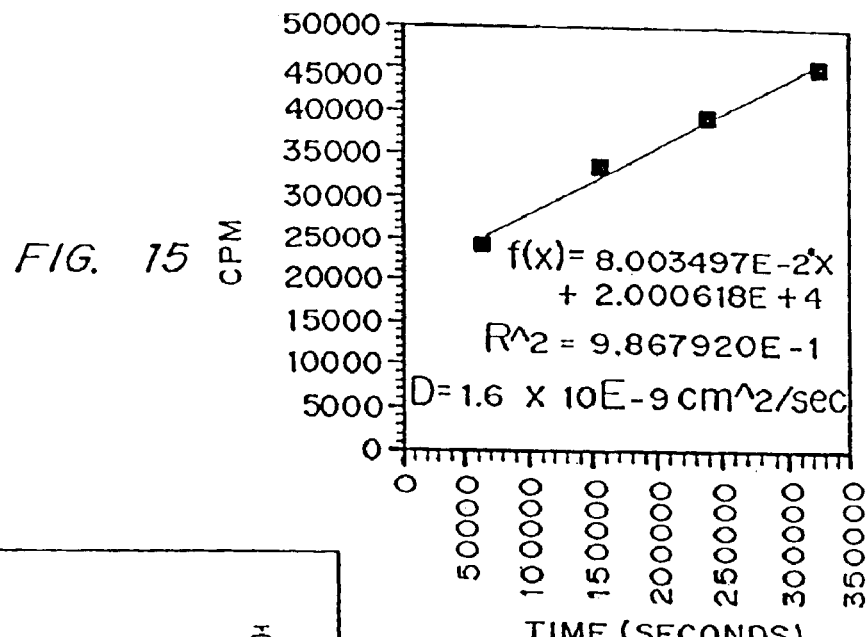

Membranes of constant thickness were prepared from neat macromers of Example 11, and used as the diffusion barrier in a two-compartment dialysis cell. FIGS. 14 and 15 show the increase in the concentration of 500 Da drug in the receptor side of the cell over time. The diffusion coefficient calculation was based on the following relationship:

$$D=J/(A^*(\Delta C/\Delta\chi)$$

where D is the diffusion coefficient, J is the measured flux, A is the exposed area of the film, ΔC is the concentration gradient across the film and Δχ is the average film thickness. The diffusion coefficients for macromers having 50% (P105L5A2) or 90% (L81L5A2) relative hydrophobic domain and were calculated to $1.6\times10^{-9} cm^2/sec$ and $5.63\times10^{-10} cm^2/sec$, respectively. Thus, diffusion was faster in the more hydrophobic material, as expected for a drug of low water solubility.

EXAMPLE 13

Release of Tetracycline and Taxol

Figure 16:
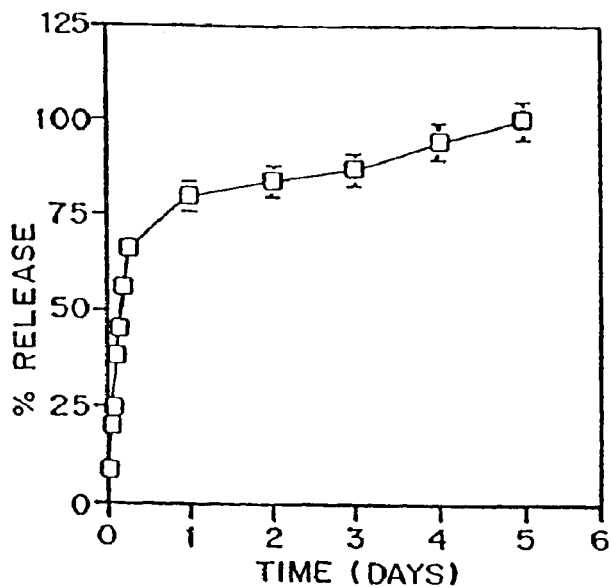
FIG. 16 is a graph showing the release of tetracycline from a hydrogel formed from monomers including a biodegradable region.

A 30% w/w solution of F127 trimethylene carbonate acrylate (as described in Example 3) in phosphate buffered saline, pH7.4 was prepared 3000 ppm Darocur® (Ciba Geigy) was incorporated in the solutions as photoinitiator. Tetracycline (free base, crystalline, F.W. 444.44) was incorporated in the macromer solution by equilibration for 12 hours at 37 degrees C. Then, 200 microliters of the solution was crosslinked by UV light (10 W/cm2, full cure). In vitro release of tetracycline from the 200 microliter cured gel, after a brief rinse, was carried out in 5 mls PBS, pH 7.4, 37° C. The PBS was exchanged daily to ensure "sink" conditions. The release profile is seen FIG. 16. After an initial burst, tetracycline was released steadily for nearly a week.

Taxol was incorporated into gels by similar procedures, except that Tween™ surfactant was used to solubilize the Taxol concentrate. A similar release pattern to that seen with tetracycline was observed.

EXAMPLE 14

Urethane-Containing Macromers

PEO of molecular weight 1450 was reacted with approximately 1 mole of lactide per end, using procedures described above, to give 1.4KL2. The 1.4KL2 was weighed into a 100 ml flask (8.65 g) and 270 ml of dried toluene was added About 50 ml of toluene was distilled off to remove residual water as the azeotrope, and the solution was cooled. Then 0.858 g (825 microliter) of commercial 1,6 hexane-diisocyanate was added, and also 1 drop of dibutyltindilaurate (ca. 0.02 g). The solution was at 60 degrees at addition, and warmed to 70 degrees over about 10 minutes. Heat was applied to maintain the solution at about 75 degrees for about 3.5 hours NMR and IR spectra confirmed consumption of the diisocyanate, and the resulting solution was therefore expected to contain alternating PEO and hexane blocks, linked by urethane linkages, and terminated by hydroxyls. This material can be capped with reactive end groups, optionally after further extension with hydroxy acids, to form a reactive macromer. The urethane links and hexane blocks are present to promote tissue adherence.

Modifications and variations of the present invention will be obvious to those skilled in the art from the foregoing detailed description. Such modifications and variations are intended to come within the scope of the following claims.

What is claimed is:

1. A method for controlling the rate of delivery of a biologically active material, comprising mixing the active material with a solution or suspension of a gel-forming macromer and covalently crosslinking the macromer to form a gel, wherein the macromer comprises at least four covalently linked polymeric blocks, at least one thermally sensitive region, and at least one covalently crosslinkable group, and wherein at least two of the blocks are hydrophobic, and at least two of the blocks are hydrophilic, and wherein the gel has a temperature dependent volume.

2. The method of claim 1 wherein the volume of the gel decreases upon an elevation in temperature.

3. The method of claim 1 wherein at least one hydrophobic block aggregates in aqueous solution to form a hydrophobic domain.

4. The method of claim 3 wherein the hydrophobicity of the domain is controlled by selecting the hydrophobicity of the block.

5. The method of claim 1 wherein the gel-forming macromer is provided in an aqueous solution or suspension.

6. The method of claim 1 wherein the biologically active material is in the form of microparticles.

7. The method of claim 1 wherein the gel is formed of microparticles.

8. The method of claim 1 wherein the biologically active material is a synthetic inorganic compound, an organic compound, a protein, a peptide, a polysaccharide, a lipid, a ganglioside, or a nucleic acid.

9. The method of claim 1 wherein the macromer further comprises biodegradable blocks.

10. The method of claim 9 wherein the gel is provided in a carrier suitable for parenteral administration.

11. The method of claim 1 wherein the macromer is crosslinked by photopolymerization.

12. The method of claim 1 wherein the macromer is applied to tissue in a pharmaceutically acceptable carrier prior to crosslinking.

13. The method of claim 1 wherein the macromer or gel is provided in a pharmaceutically acceptable carrier for parenteral administration.

* * * * *